(12) United States Patent
Laramore

(10) Patent No.: US 6,705,556 B2
(45) Date of Patent: Mar. 16, 2004

(54) COMPOSITION AND METHOD FOR INDUCING TOLERANCE TO VIRAL INFECTION IN AQUATIC ANIMALS

(75) Inventor: Charles Rolland Laramore, Vero Beach, FL (US)

(73) Assignee: First Republic Corporation of America, New York, NY (US)

( * ) Notice: Subject to any disclaimer, the term of this patent is extended or adjusted under 35 U.S.C. 154(b) by 19 days.

(21) Appl. No.: 10/115,653

(22) Filed: Mar. 28, 2002

(65) Prior Publication Data

US 2003/0049275 A1 Mar. 13, 2003

Related U.S. Application Data

(60) Provisional application No. 60/279,890, filed on Mar. 29, 2001.

(51) Int. Cl.$^7$ .............................. A01N 63/00; C12Q 7/01
(52) U.S. Cl. ................ 242/93.6; 424/204.1; 435/235.1; 435/236; 435/238; 435/239; 530/826
(58) Field of Search .............................. 435/235.1, 236, 435/238, 239; 530/826; 424/204.1, 93.6

(56) References Cited

U.S. PATENT DOCUMENTS

2003/0092145 A1 * 5/2003 Jira et al. ................ 435/173.3

OTHER PUBLICATIONS

Jory, "Shrimp Whitespot Virus In the Western Hemisphere", *Aquaculture Magazine*, vo. 25, No. 3, (May/Jun. 1999).*

Flegel, T.W. and Alday–Sanz, V., J. Appl. Ichthyol., 1998; 14:269–273.

Flegel, T.W. and Pasharawipas, T., Active Viral Accomodation: a new concept for crustacean response to viral pathogens, 1998; pp. 245–250.

Pasharawipas, T., et al., Shrimp Biotechnology in Thailand, pp. 45–53.

* cited by examiner

*Primary Examiner*—Jeffrey Stucker
(74) *Attorney, Agent, or Firm*—Darby & Darby

(57) ABSTRACT

The White Spot Syndrome Virus (WSSV) is a virus affecting shrimps as well as other crustaceans, and the WSSV epidemic poses a serious threat to the shrimp farming industry. The present invention relates to compositions and methods for inducing tolerance and/or immunity to White Spot Syndrome Virus infections. In one embodiment, the invention provides for a tolerine composition based on inactivated viral particles. In another embodiment, the invention provides for a method for inducing tolerance/immunity in shrimps by exposing larval shrimps to the tolerine composition. In yet another embodiment, the invention provides for tolerine composition with improved purity.

30 Claims, 4 Drawing Sheets

PCR RESULTS

LANE

| Lane | Sample I.D. | Results |
|------|-------------|---------|
| 1 | Prototype V-15 (HydroStat) | Positive OK |
| 2 | Prototype v-15 (1:50) | Positive OK |
| 3 | Prototype V-15 (1:100) | Positive OK |
| 4 | Positive Control | Positive |
| 5 | Negative Control | Negative |
| 6 | Molecular Wt. Ladder | OK |

COMPOSITION AND METHOD FOR INDUCING TOLERANCE TO VIRAL INFECTION IN AQUATIC ANIMALS

This application claims the priority of U.S. Provisional Application No. 60/279,890, filed on Mar. 29, 2001, which is hereby incorporated by reference in its entirety.

FIELD OF THE INVENTION

The present invention relates to compositions and methods for reducing mortality of cultured marine and freshwater (crustacean) animals due to viral infections. More specifically, the invention relates to compositions and methods for inducing tolerance against infections caused by viruses such as the White Spot Syndrome Virus in crustaceans.

BACKGROUND

As the demand for food throughout the world increases, a great deal of effort has been expended finding ways to more efficiently produce food, both animal and vegetable, to satisfy the demand. Sea life, including crustaceans and fish, has long been a source of high quality protein for human consumption. However, the activities of the wild marine product industries have, in recent years, been severely restricted because of environmental contamination problems and overfishing. Fish catches have become much smaller and it has been difficult to keep fishing grounds productive.

Attempts have been made to grow monocultures of aquatic animals (e.g., shrimp farming) under varying levels of controlled conditions. Often such farms provide a large proportion of a particular kind of seafood consumed. For example, approximately half of the penaeid shrimp consumed in the United States in 1993–94 were from farms. Aquaculture systems of the prior art (or mariculture systems, for sea-born animals) are either open (i.e., water is constantly replenished from an outside source) or closed (i.e., the same water is recirculated through the system).

Successful mariculture has been undertaken mainly in coastal areas using estuarine or coastal waters which are rich in nutrients provided by effluents from the land. Efficient production of crustaceans, fish, and shells have been undertaken by surrounding part of a marine area such as a calm gulf, a lake or an estuarine river having favorable conditions with nets, or by building ponds on land which take advantage of the tidal flow from the sea or the natural flow of water from rivers or estuaries. Large shrimp farms have thus been built in the coastal zones of Latin American and Southeast Asian countries. These shrimp culture systems rely partially on the eco-systems and marine food chains that develop in the breeding ponds to supply the feed for the shrimp. In certain cases, natural foods produced in ponds are supplemented by shrimp feed or the natural food chains are stimulated by the addition of fertilizer.

Unfortunately, shrimp and other crustaceans are susceptible to infection by a variety of viral and bacterial pathogens, such as parvoviruses, baculoviruses, Vibrio, and necrotizing hepatopancreatitis bacterium. The lack of an immune response of Crustacea to viral disease is well documented (Arala-Chaves & Sequeira (2000)), and viral infections result in significantly reduced yields of the cultured animals. In particular, one such pathogen, the White Spot Syndrom Virus (WSSV), poses a serious threat to shrimp farming industries. The WSSV is particularly virulent, the resulting infection has a high mortality rate, and the virus a wide range of potential hosts, including several species of penaid shrimp, crabs, and freshwater prawns. For instance, Flegel and Alday-Sanz (1998) documented the presence of WSSV in thirty-three different species of Crustacea in Asia. Moreover, crabs and planktonic shrimps which are common inhabitants of shrimp ponds can serve as asymptomatic carriers.

WSSV possibly originated in China in 1993, subsequently spread to the rest of Asia, and reached the eastern United States and the Western Hemisphere in 1995–1996. With few exceptions, the epidemic resulted in catastrophic mortality of shrimp, spreading rapidly among shrimp farms in every affected area. Later, in early 1999, it was detected in Central America and shortly thereafter in Ecuador with similar effects. The events of the past few years have shown that semi-intensive shrimp culture systems that dominate the industry in the Western Hemisphere, in particular those based on *Penaeus vannamei*, are highly vulnerable to the epizootic WSSV infection. The negative commercial consequences are by far the most serious threat that has ever confronted the industry, and the only measures available to minimize expected losses are those of prevention, including, e.g., virus screening of broodstock and larvae, and widespread utilization of semiclosed or closed cultivation (see, e.g., U.S. Pat. Nos. 5,947,057 and 5,732,654).

Curiously, as noted by Pasharawipas et al. (1997) and Flegel and Pasharawipas (1998), the intensity of many viral epidemics, including monodon baculovirus (MBV; which targets the hepatopancreas), immune hepatopancreatic and hematopoietic necrotic virus (IHHNV), yellow-head virus (YHV) and WSSV, have a tendency to diminish in intensity in roughly two to three years. Mechanisms such as genetic selection for resistance in the host shrimp and attenuation of the virus did not provide a plausible explanation for this phenomenon in view of the relatively short time available for these mechanisms to develop in nature. Instead, several other observations pointed to another mechanism being at work. First, the presence of innocuous viral infections was noted in many histological samples of animals with active viral infections. Several instances of viral infection without an inflammation in the tissues characterizing lethal infection are documented in shrimp and other Crustacea. Second, ample evidence of endemic IHHNV in *P. monodon* without inflammatory and lethal infection suggested a means by which a population might coexist with a virus over a long period of time. This coexistence might then allow genetic selection in the host and attenuation of virus might result in long term accommodation between the two organisms. Third, animals previously exposed to virus seemed to resist infection whereas "naive" animals without a history of previous exposure where highly susceptible to lethal infections when challenged by YHV. A similar response was observed when virus-free *P. stylirostris* were exposed to apparently healthy *P. stylirostris* that had been reared previously in the presence of the virus. The "experienced" animals were shown to be carriers of an active viral infection that proved to be lethal to the "naïve" animals.

These observations led the authors to present the "tolerance" theory (Pasharawipas et al., 1997) and later, the "accommodation" theory (Flegel and Pasharawipas, 1998), on how lethal infections are converted to innocuous infections. According to the accommodation theory, tolerance to viral infections in crustaceans is the manifestation of an active system for accommodation that is based on membrane binding involving specific memory, leading to suppression of viral triggered apoptosis and to persistent innocuous infections. It was then suggested that exposure of young larval stages to viral particles or sub-unit viral particles could result in innocuous infections rather than mortality once the animals are exposed to virus. The authors termed such a hypothetical composition "tolerine" as opposed to "vaccine", since it was theorized that these compositions would produce their effect through different mechanisms than those of vaccines.

However, so far, no such tolerine or tolerine-like composition has been produced or any beneficial effect demonstrated in a laboratory bioassay using a live virus challenge. Neither has a tolerine product applicable to routine hatchery rearing of shrimp post-larvae, or methods of successfully applying such a tolerine composition to induce protection or tolerance against WSSV infection in cultured shrimp, been presented. Thus, there is a need for new compositions and methods for reducing the impact of WSSV infection in cultured shrimp and other crustaceans. The invention addresses these and other needs in the art.

SUMMARY OF THE INVENTION

The present invention provides compositions and methods for inducing tolerance to White Spot Syndrome Virus (WSSV) in crustaceans.

The invention also provides a tolerine composition comprising inactivated WSSV. Preferably, the WSSV of the composition has been chemically inactivated, or, for example, treated at a low pH such as pH 5.6 to inactivate the virus. In one embodiment of the invention, the tolerine composition further comprises a dispersing agent and/or a preservative.

The invention also provides a method for inducing tolerance to WSSV infection in shrimps, comprising exposing the shrimp larvae to a tolerine composition. In a preferred embodiment, the shrimp larvae are substantially at the Z-1 developmental stage. In another preferred embodiment, shrimp larvae are exposed to the tolerine for at least about 30 minutes, preferably for at least about 45 minutes. In yet another preferred embodiment, the tolerine composition is admixed with shrimps in an aqueous solution. Preferably, a total of about 1 liter of tolerine is added to about 10 to about 100 liters, more preferably about 20 to about 80 liters, and even more preferably about 50 liters of shrimp solution.

DETAILED DESCRIPTION OF THE INVENTION

Figure 1:
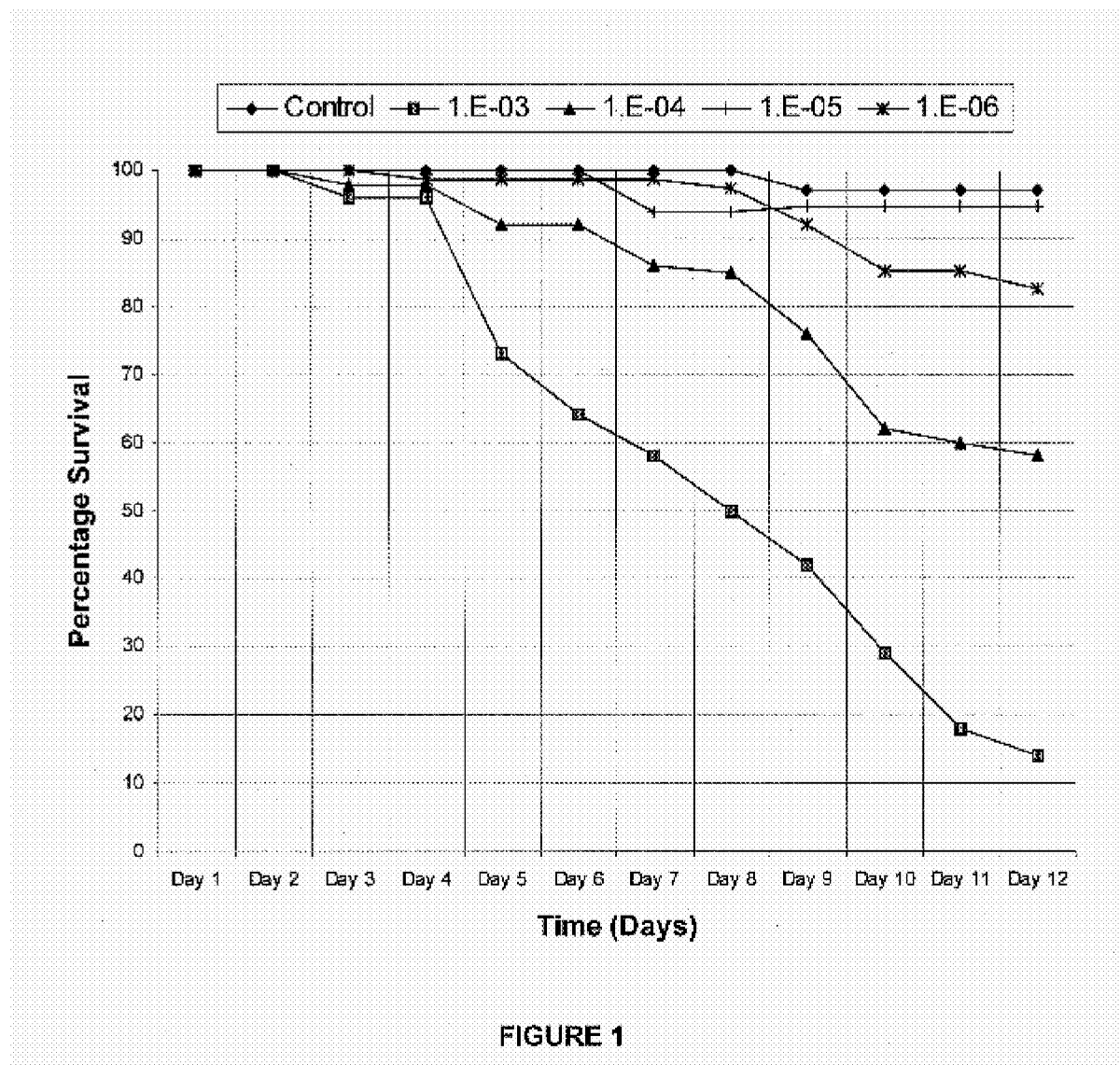
FIG. 1. Results from a typical experiment conducted to determine appropriate levels of virus to be used in subsequent viral challenge trials where tolerine-exposed animals are compared to controls. In this experiment, control animals were exposed to serial dilutions of the Viral Stock Solution (VSS).

According to the present invention, a tolerine composition can be prepared from an inactivated virus such as inactivated White Spot Syndrome Virus (WSSV). The invention also provides the application of the tolerine product in a method for inducing tolerance to a viral infection in an animal, caused by a virus such as the WSSV. For example, the present invention provides strategies for the development of tolerine products that can be applied to routine hatchery rearing of shrimp post-larvae to reduce shrimp mortality from viruses during commercial production.

Treatment with the WSSV tolerine of the invention leads to a higher survival rate than that of animals not treated with tolerine. For example, at 10 days after exposure to WSSV, the percentage of tolerine-treated animals is at least about 5%, preferably at least about 10%, more preferably at least about 20% higher than the survival of animals not treated with tolerine.

Definitions

As used herein, the term "about" or "approximately" means within 50%, preferably 25%, more preferably 10%, and most preferably 5% of the given value. Alternatively, the term "about" means the standard deviation or variance for a given value, if available.

The term "inactivated virus" means a virus rendered at least partially incapable of infecting an animal. Such inactivation of an active virus may be accomplished by, e.g., treatment with chemical agents, or any other means known in the art. Examples of chemical agents useful for this purpose are provided below.

The term "dispersing agent", "surface-active agent", or "surfactant" means a compound or mixture of compounds which lowers the surface tension of a solution, and/or disperses compounds in a solution. Another term which may be used in this context is "adjuvant". For example, a dispersing agent can reduce interactions between contaminants and viral particles in a tolerine composition. Examples of agents which may be used as dispersing agents include Tween 80, and Arlacel A.

The term "preservative" means a compound or mixture of compounds having at least one of the properties of increasing the stability of, maintaining the activity of, or preventing bacteria (sterilant) or bacterial proliferation in, the tolerine composition of the invention. A preservative may, for example, act as an antioxidant. Preferred preservatives are those which act as bacteristats (i.e., prevents growth of bacteria), and/or bactericides (i.e., kills bacteria). Examples of such preservatives include β-propiolactone (Betaprone), thimerosal, propylene glycol, and HydroStat™.

The term "supernatant" means a reasonably clear solution or suspension separable from one or more solid components having a specific size or weight. The supernatant can be separated from the solid component(s) by passage through a filter or screen having a specific cut-off size, by gravity (allowing solid components of a certain minimum weight to settle), or by centrifugation.

The term "shrimp larva" means a shrimp at least one of the following developmental stages and their associated substages: nauplius, zoea and mysis. Nauplii is the first stage following emergence from the egg, and contains five substages. Shrimp larvae are in the nauplii stages for about 48 hours depending on environmental conditions such as temperature. Protozoae (often abbreviated "Zoae") is the second stage following the nauplii stage, and contains 3 substages lasting for a total of about 4 days. Mysis is the third stage following Protozoae, and also contains 3 substages lasting for about 3 days. The shrimp larvae metamorphous into postlarvae after the mysis stage. These developmental stages are well known in the art.

The term "inducing tolerance" to a viral infection means to take measures to render an animal at least partially tolerant to infection with the virus, so that the animal exhibits no or reduced symptoms of a response to viral challenge. A preferred, but non-limiting, response is an immune response. Examples of such induced tolerance and its features are described in Flegel and Pasharawipas (1998) and Pasharawipas (1997).

An "effective amount" is an amount of a composition which, when administered to an animal, has a desired effect on the animal. For example, an effective amount of a tolerine composition for administration to shrimp larvae is an amount that induces tolerance to a virus in the animals.

A "tolerine" is a composition which, when administered to animals, can induce tolerance to a viral infection.

A "control population" is a population of shrimps that has not been exposed to a tolerine composition or to WSSV.

Preparation of Tolerine

In this section, the preparation of the tolerine composition of the invention is described. Various embodiments of this description is set forth in Examples 1 and 4–7. Although primarily intended for the preparation of a WSSV tolerine, the procedure may be generally applied to the preparation of a tolerine based on any virus attacking marine animals or crustaceans. Preferably, the source of the viral material for tolerine preparation is autogenous, or from the same origin as the animals to which it is to be applied, and includes processing of one or more primary target tissues of the virus.

Isolation of the Virus. Carapace and, preferably, hepatopancreas from infected shrimps are removed, since the hepatopancreas contains hydrolytic enzymes which can degrade viral DNA. Infected tissue can be processed by blending the tissue with a surfactant such as Arlacel A in water, saline solution, or a buffer. The amount of tissue depends on the viral content of the tissue. In general, the amount of tissue processed per liter solution is from about 10 g to about 100 g, preferably from about 20 g to about 60 g, and, even more preferably, from about 30 to about 45 g.

The tissue is the thoroughly homogenized for at least one minute, preferably at least two minutes, to effect release of the viral particles from the tissue. The homogenized tissue can then be centrifuged or filtered to remove insoluble tissue. Filtration is preferably conducted using one or more filters or screens having a cut-off size from about 500μ to about 0.1μ, preferably 300μ to about 0.3μ, and, even more preferably, about 150μ, to obtain a virus solution. For example, the virus solution can be filtered through a 105μ screen, or, more preferably, through a screen of at least about 140μ. Alternatively, the virus can be isolated and purified using sucrose gradient centrifugation, or other techniques known in the art for virus isolation and purification.

Precipitation. In one embodiment, the surplus of unnecessary proteins in the viral solution can then be precipitated. Any precipitation method known in the art which does not compromise the efficiency of the tolerine composition, and does not render the tolerine composition harmful to the animals for which it is intended, can be used. In a preferred embodiment, precipitation is achieved by allowing particles which pass through a screen or filter having a cut-off size of more than 105μ, preferably more than 150μ, to remain in the viral solution (e.g., by not using a screen smaller than about 105μ or 150μ, respectively, during prior processing steps). These particles can serve as suitable "precipitation nuclei". The viral solution is frozen to at least −20° C., and slowly thawed. For optimal precipitation, it is important not to disturb the solution during thawing, or the subsequent precipitation step. The precipitate can be allowed to slowly form and settle on the bottom of the vial in which the solution is kept. The supernatant, containing viral particles with a lesser amount of unnecessary components is then retrieved by centrifugation followed by decanting, or by filtration though a suitable filter to remove the precipitate.

Replicating the virus. If desired, the isolate obtained can be injected into hosts to allow for replication. The amount of isolate to be injected is advantageously established experimentally on a case-to-case basis, based on the properties of the isolate and the virus in questions. In the case of WSSV, the isolate may be injected into juvenile *Penaeus vannamei*. After a sufficient time of incubation, generally a couple of days after injection, hemolymph can be drawn from moribund animals. The extract can be mixed with a suitable cryopreservative such as, e.g., mannitol, and stored in a freezer, preferably at about −80° C. When needed, the extract can be used for initiating multiplication of the virus in additional trials, or for preparation of tolerine composition.

Viral inactivation. The virus in the tolerine preparation can be rendered inactivate (i.e., incapable of producing an infection) by a variety of means during any of the production steps described. A large portion of the virus particles become inactivated during the extraction procedure, especially if processed or stored at room temperature. Degradation enzymes present in tissues are released during tissue processing, which can degrade one or more components of the virus. In one embodiment, the virus can be inactivated by storage in a low pH solution, e.g., at a pH equal to or lower than about 5.6. This may be accomplished by using, e.g, a dilute HCl solution, or by adding a bacteristat such as β-propiolactone, which lowers the pH of the solution. In other embodiments, the virus is inactivated by heating or by irradiation. Propylene glycol can also be used to inactivate the WSSV virus. In yet another embodiment, the virus is inactivated by the addition of a compound that in itself renders the virus inactive, i.e., a virucide. In a preferred embodiment, an effective amount of such a virucide to inactivate the virus in a tolerine composition has little adverse effect on, or is harmless to, shrimps or shrimp larvae. In another preferred embodiment, the virucide is also a bactericide or bacteristat. Hydrostat is a preferred virucide/bacteristat. An important consideration for the choice of chemical inactivation method is that it should preserve the surface antigens of the virus upon which the tolerine is based.

The tolerine can also be prepared together with an "extender", i.e., a feed product, by mixing or administering the tolerine together with a feed product. Typically, a tolerine-extender product can be prepared by homogenizing thirty grams of infected shrimp tissue and adding the homogenate to about 300 grams of "Larval Blend Z" (a zoae diet available from Bonney, Laramore & Hopkins, Inc.) Next, the mixture is blended with 700 ml of physiological saline before refrigerating. The composition can be irradiated to receive about 2µ-rads.

In a preferred embodiment, the tolerine composition is prepared by mixing about 30 to about 45 grams of WSSV infected moribund or recently dead shrimp with one liter of physiological saline solution (PSS), adding 1 to 2 ml of Arlacel A, and homogenizing for at least one minute in a homogenizer or cell-disruption type of equipment. The homogenate is then filtered through a filter having a cut-off size of about 150µ, and this first supernatant frozen solid. Thereafter, the first supernatant is thawed (undisturbed), and any precipitate allowed to form and settle, preferably in room temperature. The second supernatant can then be decanted after the precipitate has settled to the bottom of the container. Any remaining precipitate can be removed by simple filtration or centrifugation, and discarded. The pH of the third supernatant retrieved is then adjusted to about 9.

Tolerine Composition

The preparation method described above yields a tolerine composition according to the invention. The composition may be further analyzed for, e.g. the presence of bacteria, or modified and/or complemented with other components.

Product analysis. At this stage, the identity, purity, and virus concentration of the isolate can be established using any means known in the art such as, e.g., PCR titration. PCR titration may be conducted using one or more of the following steps: (1) making a dilution series of a tolerine preparation; (2) amplifying viral DNA for each dilution by PCR using identical conditions for each dilution batch; (3) separating the components in each batch of amplified DNA using gel electrophoresis; (4) quantifying the intensity/amount of DNA present in the band corresponding to inactivated viral DNA; and (5) comparing the intensity/amount of DNA present in the bands to a control. The control can be a sample containing a known amount of inactivated viral particles, a sample which can be correlated to a certain amount of inactivated viral particles, or a sample known to have a suitable tolerine effect.

If desired, a cryoprotectant such as mannitol, DMSO, or glycerin can be added and the product frozen at −80° C. until further use.

The tolerine product can also be mixed with an dispersing agent to enhance the immunological response to the tolerine in animals exposed to the product. Suitable dispersing agents include, but are not limited to, surface active agents such as Tween-80 and Arlacel A.

Furthermore, to preserve the integrity and/or activity of the tolerine composition, preservatives may be added. Examples of suitable preservatives include, but are not limited to β-propiolactone, thimerosal, propylene glycol, and HydroStat™, or any other suitable bacteristat. Additionally, the tolerine product can be irradiated using, for example, a $^{60}$Co source, to inactivate the virus and to sterilize the composition from bacteria. In a preferred embodiment, the preservative is HydroStat. Hydrostat has the advantage that it can serve both as a virucide and bacteristat, and has been found to be very well tolerated by shrimp larvae. Thus, preferably, about 10 and about 12 ml of Hydrostat is added per liter tolerine solution, and allowed to inactivate virus and any bacteria for at least 24 hours before use.

It has also been found that the pH in the tolerine product is of importance for, e.g, stability, physical characteristics, and inactivation of the virus. Tolerine compositions in which the pH has been adjusted to near neutral (about 7) before bottling, have been shown to have sufficiently preserved tolerine activity. However, raising the pH to above about 7, preferably to at least about 8, more preferably to at least about 9 prior to bottling can reduce the amount of precipitate present, thus improving the potency of the tolerine as compared to lower pH tolerine compositions, since a precipitate can reduce the concentration of inactivated viral particles in solution by ionic interactions.

Application of the Tolerine Composition

According to the present invention, a tolerine composition based on inactivated WSSV particles can be applied in methods for inducing tolerance to WSSV infection in crustaceans. Example 2 describes one such suitable protocol for inducing immunity or tolerance to WSSV infection. A general "tolerization" protocol can be outlined as follows.

The animals to be exposed to the tolerine material are advantageously kept in a container, such as, e.g., a tank. The tolerine material is added to the container either before or after the addition of the animals. For example, in the case of cultured shrimps, the tolerine product can be applied in a small-volume holding container suspended in a large-volume tank. In a preferred embodiment, both the animals and the tolerine material are kept in aqueous solution to facilitate uniform mixing of the two. Mixing of the animals and the tolerine material can be accomplished, e.g., by simply allowing the tolerine composition to diffuse throughout the aqueous solution, by gentle stirring, or by utilizing processes such as aeration to stir the mixture. Next, the animals are exposed to or "bathed" in the tolerine containing aqueous solution for a suitable period of time. This time period may be predetermined, based on prior investigations, or determined experimentally. Preferably, the animals are incubated for at least about 30 minutes, more preferably for at least about 45 minutes, and even more preferably for at least about 2 hours. Alternatively, samples of the animal solution may be analyzed at certain intervals to evaluate a chosen property, and the incubation terminated when this property has reached a certain value. For example, the animals may be analyzed for the proportion of animals being at a certain developmental stage. Moreover, the animals may be evaluated for an effect of the tolerine exposure which affects their activity, swimming motion, or feeding in the Z-1 stage. Termination of the tolerine exposure can generally be implemented by removal of the tolerine product or dilution of the incubation solution.

For optimal tolerization effect, the animals can be exposed to the tolerine product at an early developmental, or larval, stage. Flegel and Pasharawipas (1998) suggested that their hypothetical tolerine should be applied to shrimp larvae during their transition between the naupliar and zoeal stages. Exposure of shrimps to the tolerine product of the invention is preferably initiated before a predetermined percentage, e.g., 5% or less, of a population of shrimp larvae has reached the zoea stage, and after a predetermined percentage, e.g., 95% or more, are in the naupliar stage. Alternatively, tolerization should be planned so that shrimps are exposed to the tolerine at an early Z-1 stage, or at the transition phase between the N5 and Z-1 stages.

The amount of tolerine composition to apply to either a predetermined number, biomass, or concentration of animals can be predetermined, based on prior investigations, or determined experimentally. A suitable tolerine amount to be added is an amount which is effective in inducing immunity, tolerance, or other protection against a viral infection. If the animals are in an aqueous solution, the amount of tolerine product to be applied is generally, though not necessarily, based on an estimated concentration of the tolerine product if uniformly mixed with the animal solution. In one embodiment, an amount of tolerine product effective to induce tolerance to viral infection is about 0.5–2 liters applied to 1–3 million animals or 10–100 liters of animal solution. In preferred embodiments, about 1 liter of tolerine product is applied per 1.5 million animals or 50 liters of animal solution. The use level is generally related to the number of virus particles or fragments that are added to the shrimp solution. Therefore, for tolerine batches produced via modified methods leasing to higher or lower viral particle concentrations, a suitable amount of tolerine to be added should be determined empirically using, for instance, the viral challenge assays described herein.

In one embodiment, the tolerine is administered to larvae by use of a "tolerine extender" as described above. Experiments comparing tolerine alone, extender alone, and a tolerine-extender mixture showed that the effect of the tolerine was improved when administering together with an extender.

Post-Tolerine Application Treatment

After exposure to the tolerine composition as described above, animals can be transferred to or released into a standard container or rearing tank. Standard rearing and feeding protocols known in the art,may then be used to culture the animals until harvesting. Detailed descriptions of shrimp and shrimp larvae rearing can be found in, e.g., the "CRC Handbook of Mariculture" (1983), and in the "Laboratory Manual for the Culture of Penaeid Shrimp Larvae" (1993) (see "Bibliography").

Viral Challenge Assay

To evaluate the effect of the tolerine treatment, the animals may be exposed to the same virus upon which the tolerine product was based. General descriptions of such viral challenge assays are known in, and/or can be adapted from, the art (see, e.g., Chang et al., 1998). Such assays can be used for, for example, evaluating whether a specific tolerine product has the desired effect of inducing tolerance to viral infection. In such a viral challenge assay, control animals can be used which, e.g., (a) are exposed to virus but have not been treated with tolerine as described above, or (b) are not exposed to virus but have been treated with tolerine. Alternatively, viral challenge assay can be applied to compare different preparations of tolerine products, or to compare different variants of tolerine exposure protocols, to optimize the tolerine product and/or the treatment protocol.

The following examples are intended to describe the invention without limitation.

EXAMPLE 1

Tolerine Product Preparation

This Example describes the preparation of an autogenous deactivated tolerine from semi-purified viral (WSSV) material obtained in Ecuador. The presumptive tolerine product was then transported to Ecuador and used to treat a large proportion of the commercial shrimp stocks produced at Larfico (see Examples 2 and 3 below).

WSSV infected Ecuadorian farmed shrimp (confirmed by PCR) were used to prepare the tolerine product. Tissues from the infected shrimp were processed with a tissue homogenizer. The homogenized tissue was then centrifuged and filtered. The virus was isolated and purified using sucrose gradient centrifugation. The isolate was identified as WSSV and its purity was established by PCR analysis (DiagXotics, Inc.). This purified isolate was then injected into juvenile specific pathogen-free (SPF) *Penaeus vannamei*. Two days after injection, hemolymph was drawn from moribund animals. The hemolymph was mixed with a cryopreservative and stored at −80° C. for use in initiating multiplication of the virus in future trials. Moribund or recently expired shrimp were frozen and stockpiled until a sufficient number of animals were available for tolerine preparation.

Virus particles were released and extracted from the frozen production stock. The viruses were chemically inactivated and added to a dispersing agent at a concentration established empirically using an in-house PCR titration protocol. Preservatives were added to the tolerine product, and the product was refrigerated and kept cool.

EXAMPLE 2

Tolerine Product Application and Larval Rearing

This Example describes the exposure of shrimp larvae to the tolerine composition, and subsequent rearing. Application of the tolerine product was accomplished by bathing larvae during their transition between naupliar and zoeal stages. The treated and untreated (control) animals were reared to post-larvae using normal hatchery rearing procedures and then stocked in commercial shrimp production ponds where they were exposed to WSSV in naturally infectious conditions in that are endemic in Ecuador.

Hatchery Water Supply

Seawater for the primary water source in the Larfico hatchery is treated by mechanical filtration from well points buried beneath two meters of sand at the intake point offshore and then with pressurized activated carbon filters. In a final stage of mechanical filtration the entire culture flow passes through 10-micron cartridge filters. The water is also disinfected by ozone application at a residual dose of 0.07 to 0.10 ppm.

Nauplii Disinfection

*Penaeus vannamei* nauplii, originating from captured wild gravid females and from maturation sources, were utilized for the tolerine experiments. Nauplii were temperature acclimated, disinfected with 100 ppm iodine solution (Argentine) for 30 minutes, and thoroughly rinsed for up to 3 hours with water exchanged at a rate exceeding 400% of the volume. All water utilized for nauplius stages was passed through an additional activated carbon filter to strip the ozone residual during the disinfecting and acclimatization process.

Larval Rearing

Nauplii were initially stocked into two separate 40-liter plastic container boxes and suspended in the larval rearing tanks and filled to within about 5 centimeters of the lip of the container. These suspended boxes served to concentrate the animals for the tolerine bath application while maintaining a constant temperature. The boxes were carefully suspended in the larval rearing tank by nylon cord tied to timbers laid across the top walls of the tank. Larval rearing tank capacity is 13 metric tons. The tanks have a "U" bottom, are constructed from concrete and lined with a 1.5 mm polyethylene plastic membrane. Stocking densities are normally 1,500,000 nauplii per tank or a final stocking density of 115 nauplii/liter.

The initial larval tank stocking level for nauplii is at 6 metric tons with a stocking density of 250 nauplii/liter, which is increased daily to achieve a maximum volume of 13 mt. Nauplii for tolerine experiments were divided and stocked into the temporary plastic holding containers with constant aeration at 750,000 nauplii per container or 18,750 nauplii/liter. Alga feed consisting of Chaetocerous gracilis and Thalassiosira spp. for the containers was placed in two 15-liter plastic bags with aeration and also suspended in the tank water for temperature control prior to feeding. Each bag was added to the respective container with the nauplii 2 hours prior to the N-5/Z-1 molt phase, reaching final algae cell densities of 100,000 cells/ml.

Tolerine Product Application

A 1-liter plastic bottle of refrigerated tolerine material was utilized at a volume of 1 liter/tank or 1,500,000 nauplii to "tolerize" at the N-5/Z-1 molt stage. Each liter of tolerine material was then divided into portions of 500 ml for each of two temporary holding containers. Periodic samples were taken of the nauplii to verify a 3–5% zoea population before tolerine addition. Tolerine material was applied by pouring the solution gently over the entire surface of the container to allow homogenous mixing by the aeration. Subsequent samples were taken to study animal reaction to the tolerine and periodic observations of Z-1 percentages. The "tolerization" process was continued for two hours, at which time the molted Z-1 animals were released into the larval rearing tank with algae and the normal supplemental feeding regime. The objective of this bath procedure was to assure that the entire larvae population was exposed to the tolerine for over 45 minutes at an early Z-1 stage.

After the bath container contents were released in the tank, the larval rearing procedure was conducted according to standard routine. Water exchanges increased as the feeding regime was augmented with liquid larval diets and brine shrimp nauplii. The metamorphosis to post-larvae (PL) occurs in about 7 to 10 days depending on the hatchery water temperature.

Post-Larvae Transfer and Juvenile Rearing

Hatchery animals were transferred from the internal larval rearing tanks to 50 metric ton external concrete tanks at the PL-5 stage. Post-larval animals were harvested, counted, and transferred to the external tanks at a volume of 50 PL's/liter to finish the hatchery production grow-out process at the PL-12 stage at which time they were shipped to the shrimp farms and stocked in production ponds. Experimental tolerine treated and control tanks remained separated during this phase for continuing farm experimentation and data collection. Ten thousand experimental animals for each test group (tolerine and control tanks) were also separated and simultaneously transferred to external 50-ton tanks for later viral challenge bioassay trials commencing at the PL-30 stage.

EXAMPLE 3

Viral Challenge and Bioassay

This example describes the viral challenge assay using representative samples of the treated and untreated groups described in Example 2 (see above), withheld at the hatchery and reared separately to juveniles. Randomly selected treated and control animals between the ages of 30 to 79 days after hatching were recruited for the bioassay phase of the trials. Treated and control animals were challenged by timed exposure to a viral stock solution shown to induce high mortality rates at the applied concentration. Challenged animals and controls were held in aquaria for ten days during which daily mortality was scored and dead animals were removed. Results from the bioassay trials showed that treated shrimp had a higher survival rate than untreated shrimp, thus indicating that a tolerine product may be a potential disease management tool in commercial shrimp culture.

Viral Challenge Optimization Trials

The procedures described below required several preliminary investigations in order to arrive at satisfactory mortality levels for control shrimp. Initially, a series of viral challenge experiments without any tolerine treatments were conducted to "calibrate" the lethal effects of the VSS at various concentrations. We found that a $10^{-3}$ VSS (i.e., a×1000 dilution of the viral stock solution) produced almost 100 percent mortality in 10 days. Conversely, mortality in more diluted ($10^{-6}$) solutions was only slightly higher than unexposed controls. Subsequent serial dilution trials of this kind narrowed the 10-day $LC_{50}$ (lethal dose for about 50% of the animals) of the VSS to about $10^{-4}$. This concentration was selected as that used in the bioassay viral challenge. Results of a typical serial dilution trial are presented in FIG. 1.

The preliminary trials highlighted variability in the potency of the VSS. Although the serial dilution results indicated a direct relationship between mortality and concentration of the VSS (see Example 3 and FIG. 1), the results varied from one VSS preparation to the next. Eventually this disparity was reduced, though not eliminated, by increasing the number of animals used to prepare each batch of the VSS and by carefully standardizing the preparation procedure as described above. In addition, a key step in diminishing experimental variation occurred when a feed was used during the challenge procedure to facilitate more uniform ingestion of viral particles into the animals. Accordingly, the VSS was mixed with a liquid feed product prior to the viral challenge.

Viral Stock Solution (VSS)

The VSS preparation, viral challenge, and bioassay techniques were generally conducted according to Chang et. al. (1998), although the methodology was adapted to the requirements of this study.

A semi-purified tissue filtrate solution was extracted from infected Ecuadorian animals. A 50 μl dose of source material was injected in the third abdominal segment of 4–5 g animals that were used as subjects to replicate viral material. These injected animals were collected three days after injection while still living but in a weak and moribund condition. Preliminary research had shown that most animals had died by the fourth day. For each batch of VSS material, more than a dozen animals were injected in order minimize the possibility of selecting material without a high level of virus concentration in the tissue. The selected moribund animals were stored in a freezer at −20° C. until preparation of the VSS for each individual bioassay trial. Periodically, and as needed, a filtrate of the VSS was injected into 5 g animals (10 μl per gram of body weight) to maintain a stock of animals for preparation of VSS.

Frozen tissues for VSS were ground and blended at a time two hours before the conducting the viral challenge. The protocol for VSS preparation was as follows:

1. Shell and tail were removed and frozen (−20° C.) *P. vannamei* raw stock material prepared in the laboratory as above.
2. Tissue from infected animals was homogenized in a 1-liter Waring blender mixed with seawater in a 1:9 ratio. Ambient temperature was maintained at 24° C. Blending time was limited to 90 seconds to avoid increasing the water temperature above 30° C. A total of 12–15 animals were used for each VSS preparation.
3. The mixture resulting from item 2 was centrifuged at 1,100×g for 10 minutes.
4. The resulting supernatant from centrifugation was the full-strength viral stock solution that was subsequently diluted to the desired viral challenge concentration.
5. Twenty ml of VSS was added to 180 ml of seawater at ambient temperature to produce a $10^{-1}$ VSS concentration (i.e., ×10 dilution of the VSS stock). The procedure is repeated to produce a $10^{-2}$ concentration (i.e., ×100 dilution of the VSS stock).
6. Twenty milliliters of the $10^{-2}$ VSS was mixed with 0.5 ml of Liqualife (Cargill) liquid larval feed. Twenty milliliters of this solution was added to a plastic bucket containing 1980 ml of seawater and larvae. The final viral challenge concentration was a $10^{-4}$ concentration of the full-strength tissue preparation (i.e., ×10,000 dilution of the VSS stock solution).

Viral Challenge

The viral challenge for each treatment consisted of a two hour bath in a glass container filled with 2 liters of the $10^{-4}$ dilution of the VSS. After the challenge, each of the trial replicates was rinsed in seawater and then washed thoroughly (2 dips in new container with water). The larvae were then placed in the aquaria (plastic buckets) containing 15 liters of seawater for the 10-day bioassay under the conditions described below.

Bioassay Conditions

Containers were 20-liter plastic buckets filled with 15 liters of filtered, ozonated, and aerated seawater. Animals were fed twice daily with dry ration of 50% protein shrimp pellets, at a rate of 12% BW (body weight) daily. Feeding times were 11:00 a.m. and 8:00 p.m. Each morning from 8:00 to 10:30 a.m. each tank was siphoned, removing excess feed and feces. The siphoning resulted in a daily water exchange of 25% of the aquarium volume.

Each of the treatments exposed to viral challenge was replicated in 15 aquaria. Because mortality among the unexposed controls was rare, the controls were replicated only 5 times. A total of 12 animals, aged from 40 to about 80 days were stocked in each bucket. Care was taken to select animals of similar size during each trial, but because only two of eight trials could be conducted at a time in our limited space, the weight of the animals varied with age from about 0.2 to 0.5 grams.

Daily mortality for each of the replicates was noted and the shrimp removed. Moribund animals were treated as dead animals to avoid tank fouling and auto-infection among the animals induced by cannibalism of infected tissue. Dead and live animals were counted to find by difference the number of cannibalized animals. Salinity during the experiment was adjusted to 30 ppt. Temperatures were recorded twice a daily during the trial, and were within the range of 25 to 27° C.

Results

Initial Results

For several months trials were conducted treating larvae with several tolerine preparations, rearing them to testing size (minimum PL-30), and then exposing the treated animals and their companion controls to live virus before the bioassay period. Initially, the results were alternately promising but inconclusive or simply mute with no difference in the performance of treated and untreated animals. For example, in our third tolerine prototype product we achieved five trials in a row in which the treated animals demonstrated higher survival than untreated animals after the VSS challenge. Although the probability is only about 3% that this serial ranking of outcomes is by chance, high variability within and among the separate trial conditions demonstrated no statistically significant differences. Our third set of trials then produced an intuitive sense that the tolerine prototype had a mitigating effect on mortality but, at the same time, no significant or statistically valid proof of the phenomena could be demonstrated.

Concerned by these uncertain results, we considered several modifications of our experimental method. First the VSS potency was stabilized by the method described above (see "Virus Challenge Optimization Trials", above). In our fourth set of trials using this revised technique, we found that the fourth tolerine prototype had no significant effect in mitigating mortality but, significantly, the standard deviation of the samples in each condition plummeted from about 4.0 (of 12 animals) to about 1.7–2.3. Then, with the fifth tolerine prototype preparation, we encountered consistent and significant differences between treated and untreated animal mortality. A further improvement in the statistical validity of the trials was accomplished by increasing the number of aquaria in treated and untreated trial conditions from 10 to 15 while maintaining 12 animals per replicate.

Trial 5 Results

The bioassay results for our fifth tolerine prototype are presented in TABLE 1. The table includes the end survival results in each of the three experimental conditions tested during each trial. The trials, designated in columns 5.1 to 5.8, are listed to the right of the first column listing the individual aquaria replicates for each of the eight trials. Summary statistics for each of the conditions are calculated at the end of the experimental condition sections numbered one to three. The last segment at the bottom of the table, entitled "Statistical Evaluation," shows the calculated value for the 90% confidence interval of the mean survival for each experimental condition. If the calculated confidence interval exceeded the difference between the treated and untreated mean survival, the confidence interval was considered greater that 90%. The confidence interval for the third experimental condition, the treated but unexposed controls, was not included because the confidence interval was greater than 99% in all cases of comparison to both exposed conditions.

TABLE 1

Prototype 5.0 Survival Scores (10 day bioassay, n = 12 per aquaria)

| Condition/ Replicate | Trial No. | | | | | | | |
|---|---|---|---|---|---|---|---|---|
| | 5.1 | 5.2 | 5.3 | 5.4 | 5.5 | 5.6 | 5.7 | 5.8 |
| Treated-exposed/ | | | | | | | | |
| 1 | 8 | 3 | 5 | 5 | 4 | 3 | 11 | 3 |
| 2 | 7 | 2 | 7 | 6 | 4 | 2 | 9 | 2 |
| 3 | 9 | 4 | 4 | 9 | 8 | 8 | 7 | 5 |
| 4 | 9 | 3 | 4 | 5 | 4 | 9 | 7 | 3 |
| 5 | 10 | 4 | 3 | 8 | 7 | 7 | 4 | 2 |
| 6 | 10 | 5 | 8 | 9 | 5 | 9 | 11 | 2 |
| 7 | 2 | 8 | 9 | 6 | 6 | 9 | 12 | 3 |
| 8 | 4 | 7 | 6 | 7 | 8 | 6 | 10 | 6 |
| 9 | 0 | 0 | 7 | 6 | 5 | 9 | 6 | 4 |
| 10 | 6 | 5 | 8 | 8 | 9 | 7 | 12 | 8 |
| 11 | x | x | x | 8 | 4 | 6 | 11 | 7 |
| 12 | x | x | x | 5 | 4 | 4 | 12 | 5 |
| 13 | x | x | x | 8 | 3 | 3 | 8 | 4 |
| 14 | x | x | x | 8 | 7 | 4 | 8 | 2 |
| 15 | x | x | x | 6 | 6 | 3 | 5 | 3 |
| Total survivors | 65 | 41 | 61 | 104 | 84 | 89 | 133 | 59 |
| Mean survival per replicate | 6.50 | 4.10 | 6.10 | 6.93 | 5.60 | 5.93 | 8.87 | 3.93 |
| Mean survival (%) | 54.2 | 34.2 | 50.8 | 57.8 | 46.7 | 49.4 | 73.9 | 32.8 |
| Standard deviation | 3.47 | 2.33 | 2.02 | 1.44 | 1.84 | 2.58 | 2.67 | 1.91 |
| Untreated-exposed/ | | | | | | | | |
| 1 | 7 | 2 | 8 | 5 | 2 | 2 | 3 | 5 |
| 2 | 2 | 4 | 4 | 3 | 3 | 2 | 9 | 2 |
| 3 | 5 | 4 | 5 | 6 | 0 | 6 | 8 | 0 |
| 4 | 8 | 1 | 9 | 3 | 0 | 1 | 1 | 2 |
| 5 | 8 | 0 | 3 | 5 | 4 | 1 | 9 | 0 |
| 6 | 9 | 5 | 4 | 4 | 2 | 4 | 3 | 0 |
| 7 | 2 | 7 | 8 | 9 | 0 | 2 | 7 | 7 |
| 8 | 7 | 0 | 6 | 8 | 2 | 0 | 5 | 5 |
| 9 | 7 | 3 | 9 | 3 | 5 | 2 | 9 | 0 |
| 10 | 8 | 2 | 2 | 7 | 5 | 0 | 6 | 5 |
| 11 | x | x | x | 6 | 0 | 2 | 6 | 3 |
| 12 | x | x | x | 8 | 0 | 8 | 2 | 1 |
| 13 | x | x | x | 1 | 5 | 5 | 5 | 5 |
| 14 | x | x | x | 2 | 0 | 3 | 8 | 0 |
| 15 | x | x | x | 8 | 2 | 2 | 0 | 3 |
| Total survivors | 63 | 28 | 58 | 78 | 30 | 40 | 81 | 38 |
| Mean survival per replicate | 6.30 | 2.80 | 5.80 | 5.20 | 2.00 | 2.67 | 5.40 | 2.53 |
| Mean survival (%) | 52.5 | 23.3 | 48.3 | 43.3 | 16.7 | 22.2 | 45.0 | 21.1 |
| Standard deviation | 2.50 | 2.25 | 2.57 | 2.48 | 2.00 | 2.23 | 3.02 | 2.39 |
| Treated-unexposed/ | | | | | | | | |
| 1 | 12 | 12 | 11 | 11 | 11 | 12 | 12 | 11 |
| 2 | 12 | 12 | 12 | 12 | 12 | 11 | 12 | 12 |
| 3 | 12 | 12 | 12 | 12 | 12 | 12 | 12 | 11 |
| 4 | 12 | 11 | 12 | 11 | 11 | 12 | 11 | 12 |
| 5 | 12 | 12 | 12 | 12 | 12 | 12 | 12 | 12 |
| 6 | 12 | 12 | 12 | x | x | x | x | x |
| 7 | 12 | 12 | 12 | x | x | x | x | x |
| 8 | 12 | 12 | 12 | x | x | x | x | x |
| 9 | 12 | 11 | 12 | x | x | x | x | x |
| 10 | 11 | 12 | 12 | x | x | x | x | x |
| Total survivors | 119 | 118 | 119 | 58 | 58 | 59 | 59 | 58 |
| Mean survival per replicate | 11.90 | 11.80 | 11.90 | 11.60 | 11.60 | 11.80 | 11.80 | 11.60 |
| Mean survival (%) | 99.2 | 98.3 | 99.2 | 96.7 | 96.7 | 98.3 | 98.3 | 96.7 |
| Standard deviation | 0.32 | 0.42 | 0.32 | 0.55 | 0.55 | 0.45 | 0.45 | 0.55 |
| Statistical Evaluation | | | | | | | | |
| Mean survival difference | 0.20 | 1.30 | 0.30 | 1.73 | 3.60 | 3.27 | 3.47 | 1.40 |
| Difference (%) | 1.67 | 10.83 | 2.50 | 14.44 | 30.00 | 27.22 | 28.89 | 11.67 |
| 90% confidence interval for treated-exposed | 1.81 | 1.21 | 1.05 | 0.75 | 0.96 | 1.34 | 1.39 | 0.99 |
| 90% confidence interval for untreated-exposed | 1.30 | 1.17 | 1.34 | 1.29 | 1.04 | 1.16 | 1.57 | 1.24 |
| Age at end trial (days) | 40 | 53 | 68 | 75 | 81 | 87 | 89 | 89 |

The statistical evaluation showed that the survival of the treated animals exceeded that of the untreated condition when exposed to the $10^{-4}$ VSS. The probability of the random occurrence of this outcome in eight successive trials was about 0.04%. Examination of the confidence interval statistic corroborated that the tolerine treatment mitigated mortality caused by WSSV exposure. Trials 5.1 and 5.3 were not significant at the 90% confidence interval, but the remaining six trials yielded statistically significant results. Four trials (5.4 through 5.7) were significant at a level of 99% or higher.

Figure 2:
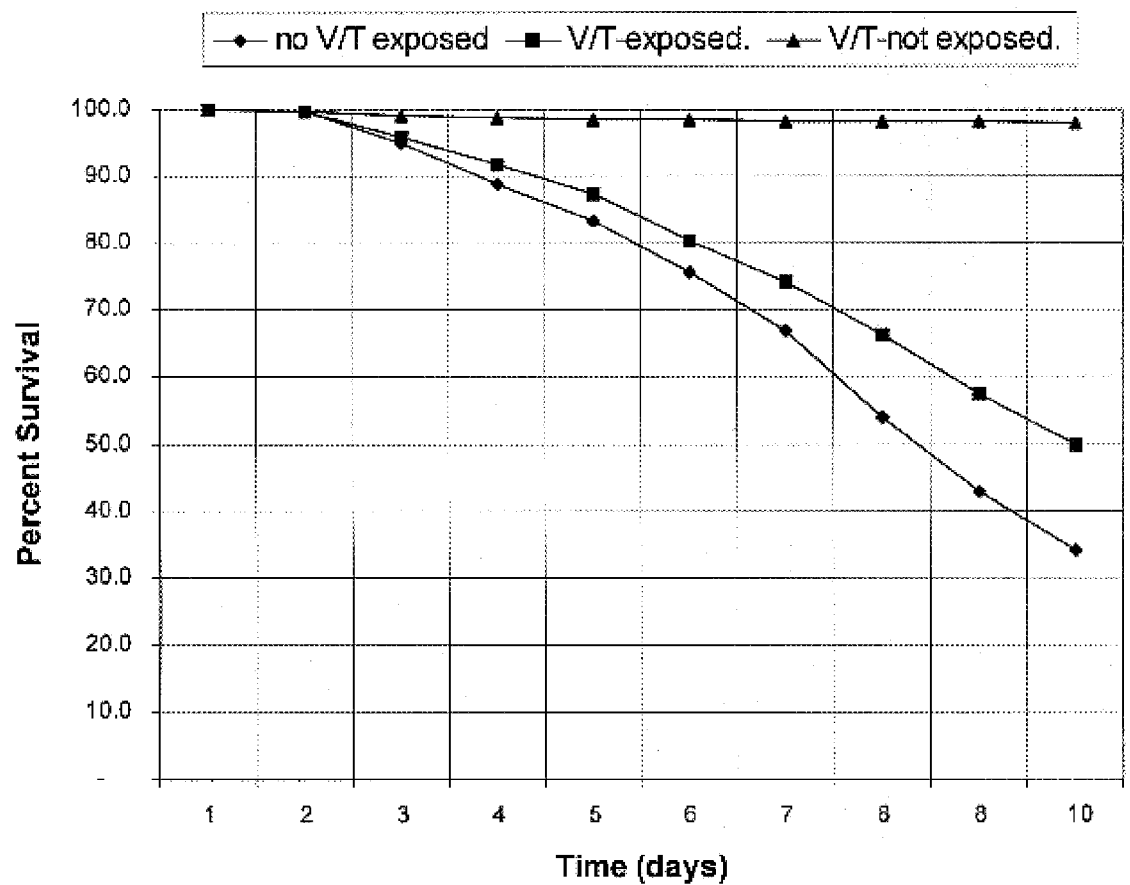
FIG. 2. Average survival pattern during a 10-day bioassay after viral challenge, comparing tolerine-treated (V/T-exposed") to control animals ("no V/T exposed"=not treated with tolerine before viral challenge; "V/T-not exposed"= treated with tolerine but not exposed to virus). The figure was based on combined data from eight trials. From 4 days after viral challenge and onwards, there was a pronounced increase in survival of the animals tolerine-treated animals over those animals not treated with tolerine. After 10 days, about 50% or the tolerine-treated animals had survived viral challenge, while only about 34% or non-tolerine treated animals had survived, representing an improvement of more than 40%.

FIG. 2 presents the average survival pattern during the 10-day bioassay, combining the data from all eight trials for purposes of showing the general mortality tendency during the bioassays.

Discussion

The results show that whatever the precise mechanism at play, early larval exposure to deactivated viral material mitigates the effect of viral infection and mortality. These experimental results thus provide substantial evidence that the accommodation hypothesis proposed by Flegel and Pasharawipas (1998) is among the likely factors in the crustacean viral disease response. The results have numerous implications to crustacean disease and shrimp farming management.

The data indicated the persistence of a single early tolerine application. In the featured prototype 5 trials, we saw the apparent tolerine effect increase as the animals aged during the course of the trials reaching a maximum result at 75 to 89 days after hatching. Other trials in progress also indicate the persistence or increase of the mitigating effect as the animals age. It may also confirm the observations of Venegas et al. (1999) that younger post-larvae may be refractory to WSSV. One might speculate that the same mechanism that triggers suppression of apoptosis in undifferentiated target tissues also accounts for the lack of infection at an early development stage.

The immediate importance of this work is as a proof of concept for a commercial tolerine product. The application of the tolerine treatment to a much larger number of commercial shrimp ponds could mitigate white spot mortality under field conditions. Field testing in an epidemic environment can be challenging in view of the difficulties in regulating the onset, titer concentration, and duration of viral exposure. The bioassay experience described herein shows that a sufficient viral titer will be lethal even to animals with a strong mitigating tolerine effect. In addition, other seasonal environmental effects, especially temperature, seem to be involved in the course and lethality of the disease. It can be surmised that the only way of dealing with the highly variable conditions expected in field trials is a large sample size. This may be a difficult enterprise requiring dozens, if not more, ponds and many months to arrive at any statistically valid demonstration of commercial efficacy.

Moreover, the tolerine composition described herein should be accompanied by multiple management techniques aimed at excluding or at least lowering the viral load in culture ponds. Micro-screening, disinfecting, and minimization of water flows are techniques that have been used successfully to diminish viral loads in culture ponds. In addition, excluding the adults and larvae of the numerous tolerant crustacean carrier species, especially those with terrestrial abilities such as many estuarine crabs such as Uca spp. and Callinectes spp, should be a primary pond management objective.

Finally, of roughly 55 ponds harvested since our trials began in early 2000, 12 were treated with tolerine products. The single most successful production pond harvested during this period with 34% survival was stocked with tolerine treated animals.

EXAMPLE 4

Tolerine Product with Bacteristat

This Example describes the production of a tolerine composition, which uses a chemical bacteristat as a preservative. In addition, the pH was adjusted to pH to at least 9.1 just after the addition of bacteristat, and prior to bottling, to enhance the physical characteristics of the tolerine product and aid in the inactivation of the virus. Previous tolerine products have used a reduction in pH to about 5.6 or below at this stage. However, under these conditions, a precipitation is formed, which settles to the bottom of the bottle. Possibly, the inactivated virus particles could be ionically attached to the tissue precipitation, thereby reducing viral uptake by the shrimp larvae.

Bacteristat

The active compound, HydroStat™, is a proprietary compound (Hydros Environmental Diagnostics, Inc.) that has antibacterial properties. HydroStat™ has not interfered with the activity of viral antigens when used in poultry vaccines.

Tolerine product was prepared from WSSV infected shrimp and analyzed using the following methodology:

Multiplication of WSSV

1. Feed 50 mg of WSSV infected tissue from the "Kill Box" to 10–15 gram SPF shrimp.
2. Place the infected shrimp individually into Styrofoam containers covered with a minimum of seawater and wait 3 to 4 days for the animals to become moribund.
3. Collect the moribund or recently dead animals and freeze at −20° C. until enough animals are available to make several liters of vaccine.

Preparation of Shrimp Tissue for Inclusion in Tolerine

1. Remove the carapace and hepatopancreas from the frozen shrimp and place in a blender at a ratio of 50 grams of tissue to 700 ml of de-ionized water.
2. Add 3 ml of an antifoaming compound (Arlacel A) and homogenate at high speed for 1–2 minutes.
3. Filter through a 300-$\mu$ screen to remove the larger pieces of chitinous material and discard.
4. Add 200 ml of de-ionized water and 0.1 ml of Anise oil (gives pleasant odor) to the filtrate and homogenize for about 1 minute.
5. Filter through a 200-$\mu$ screen and discard the retained material.
6. Adjust to 1 liter and filter successively through a 150$\mu$ screen until the product flows through the filter without restriction (several liters of the above can be done at one time, depending on the size of the blender and amount of tissue available).
7. Allow the preparation to sit for about 4 hours in a refrigerator while the tissue undergoes autolysis.

Preparation and Bottling of Tolerine Product

1. Remove 2 1-ml aliquots of product and store in the −80° C. freezer for PCR testing to determine the level of WSSV.

2. Dilute aliquots by 50 and 100× and extract the DNA and conduct a 2 step PCR analysis and compare the level of reaction on electrophoresis (relative). The 50× should be brighter than the positive control and the 100× slightly less.
3. Add 10 ml of HydroStat™ 50% to each liter of tolerine, Remove 2 1-ml aliquots to determine if the HydroStat™ interferes with the PCR analysis. If not, continue with the bottling of the product.

Virus Inactivation Tests

1. Remove 1 ml of tolerine and add to each of 5 100-liter tissue flasks containing postlarvae 25/40.
2. If any of the animals become moribund or dies hold for PCR testing and feed some of the remaining tissue to additional postlarvae.
3. If no mortality occurs test the surviving postlarvae for WSSV using PCR analysis.

Bacterial Analysis

1. Conduct total, gram negative and Vibrio counts after completion of the tolerine preparation.
2. Incubate tolerine for 1, 2 and 4 weeks and conduct the tests from step one to determine if bacteristatic or bactericidal activity has occurred.
3. Evaluate for evidence of bacterial degradation of tolerine (putrid odor).

Labeling

If the viral inactivation tests are negative and there are no pathogenic bacteria present in the vaccine product after the initial evaluation trials are concluded, the labels may be added to the bottles.

Results

Figure 3:
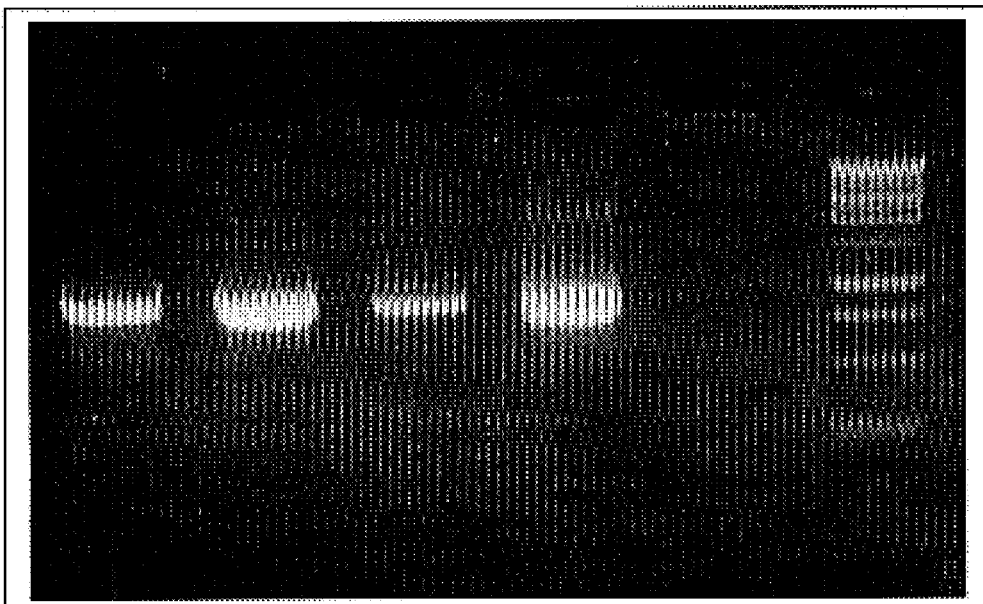
FIG. 3. PCR results from analysis of tolerine/bacteristat composition prepared at high pH.
Figure 4:
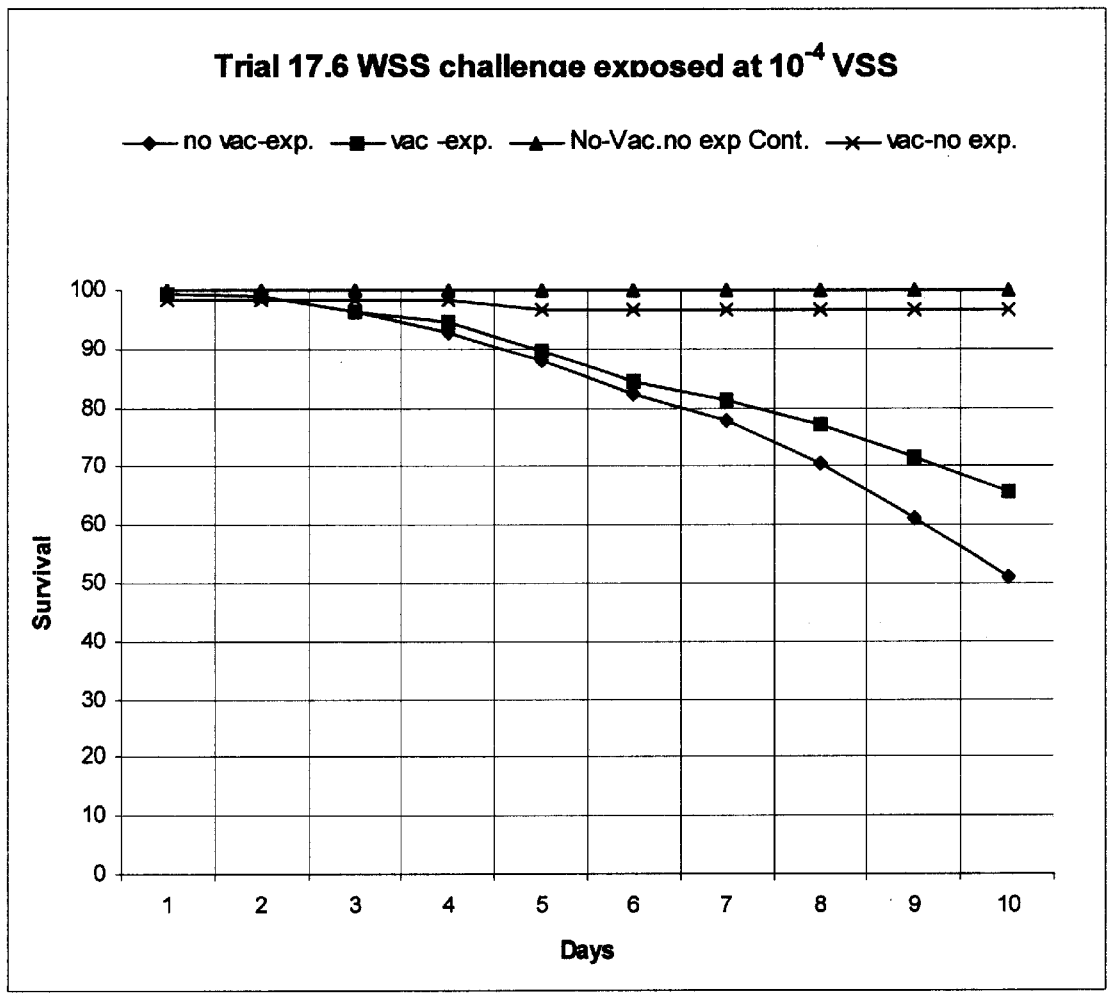
FIG. 4. Illustrative results from trial comparing survival rate of animals not treated with tolerine but exposed to virus (no vac-exp.), tolerine treated animals exposed to virus (vac-exp), tolerine-treated animals not exposed to virus (vac-no exp.) and non-treated, non-exposed controls (no-vac. no exp cont.). See Example 8.

The results from the PCR analysis are shown in FIG. 3. A single band was found in each lane to which tolerine product had been added. The results from the bacteriology test of the tolerine product were as follows:

| TPC Agar (total aerobes) | 420,000 ml |
| MacConkey Agar (Gram 1) | 260,000 ml |
| TCBS Agar (Vibrio sp.) | <1 ml |

EXAMPLE 5

Preparation of Tolerine Product

This Example describes the preparation of a tolerine product, in which VSSW was isolated by centrifugation, and the isolate analyzed for TSV, IHHNV and WSSV.

Frozen whole shrimp with the hepatopancreas removed were homogenated in a polytron tissue homogenizer after having been placed in 5 volumes of a 0.02 M Tris-buffer and 0.02 M EDTA, (pH 7.6). The homogenate was chilled to 4° C. and centrifuged at 3000×g for 20 minutes. The supernatant was re-centrifuged at 13,000×g for 30 min and the final supernatant was passed through a 0.4$\mu$ filter. Mannitol was added as a cryoprotectant at 1% and the filtrate frozen at −80° C.

The frozen viral preparations were tested for TSV, IHHNV and WSSV using PCR. The tests were negative for TSV and IHHNV and positive for WSSV. The semi-purified material (0.02 ml) was injected into 10.0 g SPF juveniles through a 0.02$\mu$ filter fitted to a syringe attached to a 27 gauge needle. Morbidity began in about 28 hours. Blood was collected from the animals and tested for WSSV using PCR and was strongly positive. The pleopods were collected from moribund animals and feed to 0.2 to 0.5 gram juveniles held in a "Kill Box". Dead or dying animals from the Kill Box were feed to large juveniles or adult animals used as virus multipliers from which viral antigen is extracted for use in preparing the tolerine. See also Sahul Hameed et al. (1998).

EXAMPLE 6

Preparation of Tolerine Product

This Example describes the preparation of a tolerine composition.

Moribund or recently expired shrimp were frozen in tap water at −20° C. until sufficient tissue (about 600 g) was available to make 15 liters of vaccine. The shrimp were thawed under tap water, the carapace removed, and the hepatopancreas excised and discarded. The tissue was placed in a blender with physiological saline solution (PSS) at a ratio of 1:5 tissue:PSS to which was added 5 ml of Arlacel A. The material was blended at high speed for 1 minute, filtered through a 300$\mu$ screen, and the chitinous material discarded. The filtrate was re-circulated through a flow-through cell in a polytron tissue homogenizer for 5 minutes. The homogenized material was then centrifuged at 5,000 rpm for 10 minutes. The supernatant (3 liters) was collected, and a 10 ml sample was taken for PCR analysis. The remainder was frozen at −80° C. until the WSSV titer could be determined.

When it had been determined that the titer was in acceptable range, the frozen material was thawed and diluted to a final volume of 14.6 liters. Glycerin (300 ml) was added and the solution was dispensed into 15 1 liter plastic bottles. A total of 1% β-propylactone was added to each bottle. The bottles were left at room temperature for 30 minutes. An equivalent amount of sterile 1 N NaOH was added to buffer the pH back to 7.6±1.2.

After 24 hrs, samples were taken and plated onto TCBS and Marine agar to test for Vibrio and other bacterial species. One ml was removed from each of five containers, and centrifuged at 13,000×g for 5 minutes. The supernatant was pooled and drawn into a 1 ml syringe to which a 0.2$\mu$ filter and a 27 gauge needle was attached. The material was then injected (0.02 ml) into each of five 12 gram shrimp to test for viral inactivation. The bottles were held under refrigeration for 7 days until the bioassay was terminated. No mortalities occurred. Blood was withdrawn from the shrimp and was tested for the presence of WSSV via PCR. All were negative. A few Spore forming bacteria (<10/ml) were detected on the Marine agar plates. No Vibrio was detected on the TCBS plates. Labels were then placed on the bottles, and the bottles delivered to Ecuador for efficacy testing.

EXAMPLE 7

Tolerine Composition with Improved Purity

This Example describes a modified method to prepare a tolerine composition discovered to induce less stress and mortality on the zoae larval stages.

The basic steps of tolerine preparation and purification were conducted as above, until the final filtration step.

1. The final filtering step on the tissue homogenate was set at 149$\mu$. The rational was that filtration at lower $\mu$, such as 105μ, can be difficult and time consuming, and, during the following steps, the larger particles of suspended protein serve as a better nucleus to form the desired precipitate.
2. The homogenate was placed in two-liter containers and was frozen in a −80° C. freezer (−20° C. works as well but would take longer to freeze).
3. The frozen homogenate was removed from the freezer and allowed to thaw at room temperature, or in the refrigerator if left overnight. It is important not to disturb the homogenate while thawing.
4. Without agitation, a precipitate was allowed to form and to settle to the bottom of the container.
5. The precipitate-containing solution was then either filtered through an appropriately sized screen to remove the precipitate, centrifuged and the supernatant decanted, or both.
6. The clear supernatant (collected by filtration and/or decanting of centrifuged product), separated from the precipitate, was placed into a container for pH adjustment and addition of the bacteristat.

Remaining steps, including packaging, can be performed as previously described.

The above procedure resulted in a much more clear solution, and PCR analysis showed that the viral level was similar to tolerine preparations not subjected to the additional treatment. Using the modified tolerine product, the pre-virus exposure mortality in vaccinated animals is reduced to levesi similar to non-vaccinated animals. The reason for this improvement is that suspended and dissolved extraneous protein in the tolerine solution could have a fouling effect on the larvae and also serve a medium to propagate harmful bacteria. Thus, the present modified method reduces the level of protein, and thereby larvae mortality, without reducing the level of antigen in and efficacy of the product.

EXAMPLE 8

Tolerine Trials

This Example reports the results of several tolerine trials, conducted according to the general procedures outlined in Examples 2 and 3.

The results represent 17 trials, each comparing animals administered tolerine by a liquid feed and exposed to VSSW ("vac+v. feed-exp") with animals given liquid feed without tolerine and exposed to WSSV ("v. feed only-exp"); animals not given liquid feed or tolerine and exposed to WSSV ("no vac-exp"), and animals given tolerine but not exposed to WSSV ("vac-no exp."). Experiments 7–8 were conducted using tolerine preparations containing Hydrostat™, and experiments denoted 17 used tolerine preparations prepared in which unnecessary proteinaceous components were precipited and removed from the tolerine.

TABLE 2

| | Days After Exposure - Percentage Survivors | | | | | | | | | |
|---|---|---|---|---|---|---|---|---|---|---|
| Group | 1 | 2 | 3 | 4 | 5 | 6 | 7 | 8 | 9 | 10 |
| Experiment 7.1 | | | | | | | | | | |
| no vac-exp. | 100.0 | 99.4 | 93.3 | 91.1 | 88.3 | 85.0 | 82.8 | 80.0 | 77.8 | 75.6 |
| vac + v. feed-exp. | 100.0 | 98.9 | 96.7 | 96.7 | 96.7 | 94.4 | 92.8 | 91.7 | 85.6 | 81.1 |
| v. Feed only exp. | 100.0 | 99.4 | 93.9 | 93.9 | 93.3 | 89.4 | 88.3 | 87.8 | 83.9 | 79.4 |
| vac-no exp | 100.0 | 100.0 | 100.0 | 100.0 | 100.0 | 100.0 | 100.0 | 100.0 | 100.0 | 100.0 |
| Experiment 7.2 | | | | | | | | | | |
| no vac-exp. | 100.0 | 96.1 | 95.0 | 92.2 | 91.1 | 87.8 | 82.8 | 77.8 | 73.9 | 69.4 |
| vac + v. feed-exp. | 100.0 | 96.1 | 85.0 | 75.6 | 65.0 | 60.0 | 55.6 | 50.0 | 45.6 | 42.2 |
| v. Feed only exp. | 100.0 | 97.8 | 93.9 | 92.2 | 88.3 | 85.0 | 84.4 | 78.9 | 72.8 | 66.7 |
| vac-no exp. | 100.0 | 100.0 | 100.0 | 100.0 | 100.0 | 98.3 | 98.3 | 98.3 | 98.3 | 98.3 |
| Experiment 7.3 | | | | | | | | | | |
| no vac-exp. | 100.0 | 100.0 | 100.0 | 100.0 | 97.8 | 91.1 | 87.2 | 83.9 | 82.8 | 80.6 |
| vac + v. feed-exp. | 100.0 | 100.0 | 100.0 | 100.0 | 97.2 | 87.8 | 85.0 | 81.1 | 79.4 | 76.7 |
| v. Feed only exp. | 100.0 | 100.0 | 100.0 | 99.4 | 98.9 | 89.4 | 83.9 | 79.4 | 78.9 | 74.4 |
| vac-no exp. | 100.0 | 100.0 | 100.0 | 100.0 | 100.0 | 100.0 | 100.0 | 100.0 | 100.0 | 100.0 |
| Experiment 7.4 | | | | | | | | | | |
| no vac-exp. | 100.0 | 98.9 | 98.3 | 97.2 | 96.7 | 95.6 | 93.9 | 91.7 | 90.0 | 88.3 |
| vac + v. feed-exp. | 100.0 | 100.0 | 97.2 | 93.3 | 91.1 | 90.6 | 88.9 | 86.7 | 86.1 | 84.4 |
| v. Feed only exp. | 100.0 | 99.4 | 97.2 | 94.4 | 94.4 | 93.3 | 92.2 | 91.7 | 91.1 | 87.2 |
| vac-no exp. | 100.0 | 100.0 | 100.0 | 98.3 | 98.3 | 98.3 | 98.3 | 98.3 | 98.3 | 98.3 |
| Experiment 7.5 | | | | | | | | | | |
| no vac-exp. | 100.0 | 100.0 | 98.2 | 88.7 | 79.2 | 72.0 | 66.7 | 63.7 | 60.7 | 56.5 |
| vac + v. feed-exp. | 100.0 | 100.0 | 100.0 | 98.2 | 82.7 | 76.8 | 64.3 | 58.9 | 54.2 | 50.0 |
| v. Feed only exp. | 100.0 | 100.0 | 99.4 | 94.0 | 86.9 | 79.2 | 71.4 | 66.1 | 61.9 | 57.1 |
| vac-no exp. | 100.0 | 100.0 | 100.0 | 100.0 | 100.0 | 100.0 | 100.0 | 100.0 | 98.3 | 96.7 |
| Experiment 7.6 | | | | | | | | | | |
| no vac-exp. | 100.0 | 98.9 | 94.4 | 87.2 | 82.8 | 75.6 | 71.1 | 68.3 | 58.3 | 50.6 |
| vac + v. feed-exp. | 100.0 | 100.0 | 98.9 | 96.7 | 94.4 | 90.0 | 88.3 | 80.6 | 76.7 | 70.0 |
| v. Feed only exp. | 100.0 | 99.4 | 98.9 | 98.3 | 95.0 | 93.9 | 92.8 | 91.1 | 87.8 | 86.1 |
| vac-no exp. | 100.0 | 100.0 | 100.0 | 100.0 | 100.0 | 100.0 | 100.0 | 100.0 | 100.0 | 100.0 |

TABLE 2-continued

| Group | \multicolumn{10}{c}{Days After Exposure - Percentage Survivors} |
|---|---|---|---|---|---|---|---|---|---|---|
| | 1 | 2 | 3 | 4 | 5 | 6 | 7 | 8 | 9 | 10 |
| Experiment 8.1 | | | | | | | | | | |
| no vac-exp. | 100.0 | 96.7 | 96.1 | 92.2 | 71.1 | 56.1 | 47.8 | 40.6 | 35.0 | 31.7 |
| vac + v. feed-exp. | 100.0 | 99.4 | 99.4 | 96.7 | 83.3 | 78.3 | 75.6 | 71.7 | 68.3 | 65.6 |
| v. Feed only exp. | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 100.0 | 100.0 |
| Experiment 8.2 | | | | | | | | | | |
| no vac-exp. | 100.0 | 100.0 | 100.0 | 100.0 | 93.9 | 88.3 | 83.9 | 79.4 | 75.6 | 66.7 |
| vac + v. feed-exp. | 100.0 | 100.0 | 98.3 | 95.6 | 91.7 | 90.0 | 85.0 | 77.8 | 76.1 | 70.6 |
| v. Feed only exp. | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 100.0 | 100.0 |
| Experiment 8.3 | | | | | | | | | | |
| no vac-exp. | 100.0 | 99.4 | 98.3 | 96.1 | 93.9 | 87.2 | 83.9 | 82.8 | 81.1 | 80.6 |
| vac + v. feed-exp. | 100.0 | 99.4 | 97.8 | 96.7 | 96.7 | 93.9 | 93.3 | 93.3 | 93.3 | 91.7 |
| v. Feed only exp. | 100.0 | 100.0 | 98.3 | 98.3 | 98.3 | 98.3 | 98.3 | 98.3 | 98.3 | 98.3 |
| vac-no exp. | 100.0 | 100.0 | 98.3 | 98.3 | 98.3 | 98.3 | 98.3 | 98.3 | 98.3 | 98.3 |
| Experiment 8.4 | | | | | | | | | | |
| no vac-exp. | 100.0 | 100.0 | 100.0 | 96.7 | 92.8 | 87.2 | 83.9 | 82.8 | 81.7 | 79.4 |
| vac + v. feed-exp. | 100.0 | 100.0 | 98.9 | 98.3 | 93.3 | 88.9 | 83.3 | 80.6 | 80.0 | 76.7 |
| v. Feed only exp. | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 100.0 | 100.0 |
| Experiment 8.5 | | | | | | | | | | |
| no vac-exp. | 100.0 | 100.0 | 100.0 | 97.8 | 93.9 | 89.4 | 87.2 | 82.2 | 78.3 | 75.6 |
| vac + v. feed-exp. | 100.0 | 100.0 | 100.0 | 98.3 | 95.0 | 91.7 | 88.3 | 86.1 | 85.0 | 81.1 |
| v. Feed only exp. | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 100.0 | 100.0 |
| Experiment 8.6 | | | | | | | | | | |
| no vac-exp. | 100.0 | 100.0 | 100.0 | 97.8 | 96.1 | 91.1 | 84.4 | 79.4 | 76.1 | 67.8 |
| vac + v. feed-exp. | 100.0 | 100.0 | 100.0 | 98.3 | 90.6 | 81.1 | 70.0 | 62.2 | 56.7 | 49.4 |
| v. Feed only exp. | 100.0 | 100.0 | 100.0 | 100.0 | 98.3 | 98.3 | 98.3 | 98.3 | 98.3 | 98.3 |
| vac-no exp. | 100.0 | 100.0 | 100.0 | 98.3 | 98.3 | 98.3 | 98.3 | 98.3 | 98.3 | 98.3 |
| Experiment 8.7 | | | | | | | | | | |
| no vac-exp. | 100.0 | 100.0 | 100.0 | 99.4 | 91.7 | 85.6 | 78.3 | 73.3 | 68.3 | 62.8 |
| vac + v. feed-exp. | 100.0 | 100.0 | 100.0 | 100.0 | 95.0 | 90.0 | 81.7 | 73.3 | 70.6 | 63.3 |
| v. Feed only exp. | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 100.0 | 100.0 |
| Experiment 8.8 | | | | | | | | | | |
| no vac-exp. | 100.0 | 100.0 | 95.6 | 84.4 | 71.1 | 67.8 | 61.7 | 53.9 | 45.6 | 42.2 |
| vac + v. feed-exp. | 100.0 | 100.0 | 96.7 | 87.8 | 77.8 | 75.0 | 66.1 | 62.2 | 52.8 | 48.3 |
| v. Feed only exp. | 100.0 | 100.0 | 100.0 | 100.0 | 100.0 | 95.0 | 91.7 | 91.7 | 90.0 | 88.3 |
| vac-no exp. | 100.0 | 100.0 | 100.0 | 100.0 | 100.0 | 100.0 | 100.0 | 100.0 | 100.0 | 100.0 |
| Experiment 11.1 | | | | | | | | | | |
| no vac-exp. | 98.3 | 96.1 | 92.8 | 88.9 | 83.3 | 78.3 | 76.1 | 71.1 | 68.3 | 67.2 |
| vac-exp. | 98.3 | 88.9 | 80.0 | 72.8 | 66.7 | 61.1 | 50.0 | 45.0 | 41.7 | 40.6 |
| No-Vac. no exp Cont. | 100.0 | 100.0 | 100.0 | 100.0 | 100.0 | 100.0 | 100.0 | 100.0 | 98.3 | 96.7 |
| vac-no exp. | 100.0 | 100.0 | 100.0 | 100.0 | 100.0 | 100.0 | 100.0 | 98.3 | 98.3 | 98.3 |
| Experiment 15.1 | | | | | | | | | | |
| no vac-exp. @ 10-4 | 100.0 | 98.3 | 87.8 | 96.7 | 95.6 | 94.4 | 93.3 | 92.8 | 92.8 | 92.2 |
| Dip-vac-exp. @ 10-4 | 98.3 | 96.1 | 92.2 | 91.1 | 90.6 | 88.9 | 88.3 | 88.3 | 86.1 | 86.1 |
| Vac + Dx-2 exp. @ 10-4 | 99.4 | 96.1 | 93.9 | 87.8 | 87.8 | 87.8 | 87.8 | 86.7 | 86.7 | 86.7 |
| Dx-2 exp. @ 10-4 | 100.0 | 100.0 | 98.3 | 92.2 | 91.7 | 91.1 | 89.4 | 86.1 | 85.6 | 84.4 |
| No-Vac. no exp Cont. | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 100.0 | 100.0 |
| Vac + Dx-2 no exp. | 100.0 | 100.0 | 100.0 | 100.0 | 100.0 | 100.0 | 100.0 | 100.0 | 100.0 | 100.0 |
| Dx-2 no exp. | 100.0 | 100.0 | 100.0 | 100.0 | 100.0 | 100.0 | 100.0 | 100.0 | 100.0 | 100.0 |
| Experiment 15.2 | | | | | | | | | | |
| no vac-exp. @ 10-4 | 100.0 | 98.9 | 97.2 | 95.0 | 92.8 | 91.1 | 87.8 | 86.1 | 82.8 | 81.1 |
| Dip-vac-exp. @ 10-4 | 94.4 | 98.9 | 97.2 | 97.2 | 97.2 | 87.2 | 94.4 | 91.7 | 91.1 | 90.0 |
| Vac + Dx-2 exp. @ 10-4 | 100.0 | 100.0 | 98.9 | 98.9 | 98.3 | 98.3 | 93.3 | 90.6 | 90.0 | 89.4 |
| Dx-2 exp. @ 10-4 | 100.0 | 100.0 | 97.8 | 96.7 | 95.6 | 95.6 | 92.8 | 92.2 | 100.0 | 90.0 |
| No-Vac. no exp Cont. | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 100.0 | 100.0 |
| Vac + Dx-2 no exp. | 100.0 | 100.0 | 100.0 | 100.0 | 100.0 | 100.0 | 100.0 | 100.0 | 100.0 | 100.0 |
| Dx-2 no exp. | 100.0 | 100.0 | 100.0 | 100.0 | 100.0 | 100.0 | 100.0 | 100.0 | 100.0 | 100.0 |

TABLE 2-continued

| Group | \multicolumn{10}{c}{Days After Exposure - Percentage Survivors} |
|---|---|---|---|---|---|---|---|---|---|---|
| | 1 | 2 | 3 | 4 | 5 | 6 | 7 | 8 | 9 | 10 |
| Experiment 15.3 | | | | | | | | | | |
| no vac-exp. @ 10-4 | 98.3 | 96.7 | 93.9 | 90.0 | 83.9 | 77.2 | 71.1 | 64.4 | 61.7 | 57.8 |
| Dip-vac-exp. @ 10-4 | 98.9 | 94.4 | 90.6 | 86.1 | 82.2 | 80.6 | 78.9 | 77.2 | 73.3 | 72.2 |
| Vac + Dx-2 exp. @ 10-4 | 99.4 | 96.7 | 95.6 | 95.0 | 93.9 | 93.3 | 89.4 | 88.3 | 84.4 | 82.2 |
| Dx-2 exp. @ 10-4 | 100.0 | 92.8 | 88.9 | 84.4 | 82.2 | 77.8 | 75.6 | 72.2 | 70.6 | 65.6 |
| No-Vac. no exp Cont. | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 100.0 | 100.0 |
| Vac + Dx-2 no exp. | 100.0 | 100.0 | 100.0 | 100.0 | 100.0 | 100.0 | 100.0 | 100.0 | 100.0 | 100.0 |
| Dx-2 no exp. | 100.0 | 100.0 | 100.0 | 100.0 | 100.0 | 100.0 | 100.0 | 100.0 | 100.0 | 100.0 |
| Experiment 15.4 | | | | | | | | | | |
| no vac-exp. @ 10-4 | 100.0 | 99.49 | 95.0 | 90.0 | 85.6 | 79.4 | 75.6 | 67.8 | 66.7 | 66.1 |
| Dip-vac-exp. @ 10-4 | 100.0 | 99.4 | 97.8 | 96.1 | 92.8 | 90.0 | 86.1 | 83.3 | 81.7 | 81.1 |
| Vac + Dx-2 exp. @ 10-4 | 100.0 | 99.4 | 96.1 | 94.4 | 90.6 | 85.6 | 82.2 | 77.8 | 76.1 | 75.0 |
| Dx-2 exp. @ 10-4 | 100.0 | 100.0 | 98.3 | 94.4 | 89.4 | 84.4 | 75.0 | 70.6 | 69.4 | 67.2 |
| No-Vac. no exp Cont. | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 100.0 | 100.0 |
| Vac + Dx-2 no exp. | 100.0 | 100.0 | 100.0 | 100.0 | 100.0 | 100.0 | 100.0 | 100.0 | 100.0 | 100.0 |
| Dx-2 no exp. | 100.0 | 100.0 | 100.0 | 100.0 | 100.0 | 100.0 | 100.0 | 100.0 | 100.0 | 100.0 |
| Experiment 15.5 | | | | | | | | | | |
| no vac-exp. @ 10-4 | 100.0 | 100.0 | 97.2 | 87.8 | 75.0 | 68.3 | 57.2 | 51.7 | 43.9 | 29.4 |
| Dip-vac-exp. @ 10-4 | 100.0 | 100.0 | 96.1 | 88.3 | 80.0 | 71.1 | 58.3 | 52.2 | 48.9 | 42.2 |
| Vac + Dx-2 exp. @ 10-4 | 100.0 | 99.4 | 97.2 | 92.2 | 82.8 | 76.7 | 72.8 | 68.9 | 65.6 | 61.7 |
| Dx-2 exp. @ 10-4 | 100.0 | 100.0 | 95.6 | 93.3 | 81.7 | 76.1 | 67.2 | 61.7 | 56.7 | 52.2 |
| No-Vac. no exp Cont. | 100.0 | 100.0 | 100.0 | 100.0 | 100.0 | 100.0 | 100.0 | 100.0 | 98.3 | 96.7 |
| vac-no exp. | 100.0 | 100.0 | 100.0 | 100.0 | 100.0 | 100.0 | 100.0 | 100.0 | 100.0 | 100.0 |
| Vac + Dx-2 no exp. | 100.0 | 100.0 | 100.0 | 100.0 | 100.0 | 100.0 | 100.0 | 100.0 | 100.0 | 100.0 |
| Dx-2 no exp. | 100.0 | 100.0 | 100.0 | 100.0 | 100.0 | 100.0 | 100.0 | 100.0 | 100.0 | 100.0 |
| Experiment 15.6 | | | | | | | | | | |
| no vac-exp. @ 10-4 | 100.0 | 97.8 | 94.4 | 87.2 | 77.2 | 70.6 | 53.9 | 43.9 | 36.7 | 31.1 |
| Dip-vac-exp. @ 10-4 | 100.0 | 96.7 | 92.2 | 87.8 | 83.3 | 75.0 | 59.4 | 47.2 | 43.3 | 35.5 |
| Vac + Dx-2 exp. @ 10-4 | 100.0 | 98.9 | 93.3 | 88.9 | 88.9 | 77.2 | 69.4 | 63.3 | 54.4 | 51.1 |
| Dx-2 exp. @ 10-4 | 100.0 | 97.2 | 90.0 | 86.7 | 86.7 | 62.8 | 41.1 | 25.0 | 16.1 | 13.3 |
| No-Vac. no exp Cont. | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 100.0 | 100.0 |
| Vac + Dx-2 no exp. | 100.0 | 100.0 | 100.0 | 100.0 | 100.0 | 100.0 | 100.0 | 100.0 | 100.0 | 100.0 |
| Dx-2 no exp. | 100.0 | 100.0 | 100.0 | 100.0 | 100.0 | 100.0 | 98.3 | 95.0 | 95.0 | 95.0 |
| Experiment 16.2 | | | | | | | | | | |
| no vac-exp. @ 10-4 | 94.4 | 89.4 | 85.6 | 83.3 | 78.3 | 68.3 | 60.6 | 53.9 | 47.2 | 41.7 |
| vac-no exp. @ 10-4 | 100.0 | 96.7 | 92.2 | 90.6 | 86.7 | 82.8 | 78.3 | 73.3 | 68.9 | 62.8 |
| No-Vac. no exp Cont | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 98.3 | 98.3 | 98.3 | 98.3 | 98.3 |
| Experiment 16.3 | | | | | | | | | | |
| no vac-exp. @ 10-4 | 100.0 | 88.9 | 83.9 | 78.9 | 70.6 | 60.0 | 55.6 | 46.7 | 40.0 | 33.3 |
| vac-no exp. @ 10-4 | 100.0 | 100.0 | 86.1 | 85.6 | 82.2 | 78.3 | 70.6 | 62.2 | 55.0 | 49.4 |
| No-Vac. no exp Cont | 100.0 | 100.0 | 100.0 | 100.0 | 98.3 | 98.3 | 95.0 | 95.0 | 90.0 | 90.0 |
| vac-no exp. | 100.0 | 100.0 | 100.0 | 100.0 | 100.0 | 100.0 | 98.3 | 98.3 | 93.3 | 93.3 |
| Experiment 16.4 | | | | | | | | | | |
| no vac-exp. | 100.0 | 88.3 | 82.2 | 77.2 | 62.8 | 59.4 | 56.1 | 54.4 | 51.1 | 45.6 |
| vac-exp. | 100.0 | 93.3 | 91.1 | 86.1 | 81.7 | 78.9 | 76.1 | 72.2 | 70.0 | 67.8 |
| No-Vac. no exp Cont | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 98.3 | 98.3 | 96.7 | 96.7 | 96.7 |
| Experiment 16.5 | | | | | | | | | | |
| no vac-exp. | 98.9 | 97.2 | 96.1 | 93.9 | 92.2 | 90.6 | 84.4 | 82.8 | 80.6 | 78.9 |
| vac-exp. | 98.9 | 96.7 | 96.1 | 92.8 | 89.4 | 88.9 | 82.2 | 80.6 | 77.2 | 75.6 |
| No-Vac. no exp Cont | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 98.3 | 98.3 |
| Experiment 16.6 | | | | | | | | | | |
| no vac-exp. | 97.8 | 95.0 | 93.9 | 90.6 | 88.9 | 83.9 | 80.0 | 75.6 | 71.1 | 68.9 |
| vac-exp. | 98.9 | 97.8 | 95.0 | 94.4 | 92.8 | 86.1 | 81.1 | 77.2 | 75.0 | 73.9 |
| No-Vac. no exp Cont | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 100.0 | 100.0 |

TABLE 2-continued

| Group | Days After Exposure - Percentage Survivors | | | | | | | | | |
|---|---|---|---|---|---|---|---|---|---|---|
| | 1 | 2 | 3 | 4 | 5 | 6 | 7 | 8 | 9 | 10 |
| Experiment 16.7 | | | | | | | | | | |
| no vac-exp. | 100.0 | 91.1 | 84.4 | 68.3 | 62.2 | 56.1 | 48.3 | 45.0 | 41.7 | 37.2 |
| vac-exp. | 100.0 | 97.2 | 94.4 | 90.6 | 86.7 | 84.4 | 80.6 | 76.1 | 72.2 | 67.8 |
| No-Vac. no exp Cont | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 98.3 | 98.3 | 98.3 | 98.3 | 98.3 |
| Experiment 16.8 | | | | | | | | | | |
| no vac-exp. | 100.0 | 96.1 | 93.9 | 90.6 | 88.3 | 79.4 | 67.8 | 61.1 | 52.2 | 46.7 |
| vac-exp. | 100.0 | 96.1 | 92.8 | 89.4 | 86.1 | 73.3 | 60.6 | 57.2 | 52.2 | 46.7 |
| No-Vac. no exp Cont | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 98.3 | 98.3 | 98.3 | 98.3 | 98.3 | 98.3 |
| Experiment 17.1 | | | | | | | | | | |
| no vac-exp. @ 10-4 | 95.0 | 91.1 | 83.3 | 82.8 | 78.9 | 77.8 | 75.6 | 74.4 | 71.1 | 68.3 |
| vac-exp. @ 10-4 | 98.9 | 95.0 | 91.7 | 91.7 | 90.6 | 87.2 | 86.1 | 83.9 | 81.1 | 77.8 |
| No-Vac. no exp Cont | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 100.0 | 100.0 |
| Experiment 17.2 | | | | | | | | | | |
| no vac-exp. @ 10-4 | 97.2 | 88.3 | 87.2 | 86.7 | 86.1 | 83.9 | 82.2 | 77.2 | 71.1 | 67.2 |
| vac-exp. @ 10-4 | 98.9 | 95.6 | 95.6 | 95.0 | 94.4 | 93.3 | 89.4 | 86.7 | 82.2 | 81.7 |
| No-Vac. no exp Cont | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 98.3 | 98.3 | 96.7 | 96.7 | 96.7 | 96.7 | 96.7 |
| Experiment 17.3 | | | | | | | | | | |
| no vac-exp. @ 10-4 | 97.2 | 96.7 | 95.6 | 90.6 | 86.1 | 80.6 | 76.1 | 73.9 | 68.3 | 63.9 |
| vac-exp. @ 10-4 | 98.3 | 96.7 | 96.1 | 89.4 | 87.2 | 86.1 | 82.8 | 79.4 | 76.7 | 75.0 |
| No-Vac. no exp Cont | 100.0 | 100.0 | 100.0 | 98.3 | 98.3 | 98.3 | 96.7 | 96.7 | 96.7 | 96.7 |
| 100.0 vac-no exp. | 100.0 | 100.0 | 100.0 | 100.0 | 100.0 | 100.0 | 100.0 | 100.0 | 100.0 | 100.00 |
| Experiment 17.4 | | | | | | | | | | |
| no vac-exp. | 100 | 94.4 | 88.3 | 82.8 | 79.4 | 76.1 | 70.6 | 63.9 | 59.4 | 56.7 |
| vac-exp. | 99.4 | 96.1 | 94.4 | 94.4 | 90.0 | 88.9 | 85.0 | 79.4 | 76.1 | 70.0 |
| No-Vac. no exp Cont | 100.0 | 100.0 | 100.0 | 100.0 | 98.3 | 98.3 | 98.3 | 98.3 | 98.3 | 98.3 |
| vac-no exp. | 100.0 | 100.0 | 100.0 | 100.0 | 100.0 | 98.3 | 98.3 | 98.3 | 98.3 | 98.3 |
| Experiment 17.5 | | | | | | | | | | |
| no vac-exp. | 100.0 | 99.4 | 95.6 | 92.8 | 85.6 | 77.8 | 71.1 | 64.4 | 60.0 | 50.6 |
| vac-exp. | 99.4 | 99.4 | 96.1 | 92.8 | 88.3 | 83.3 | 81.1 | 77.2 | 71.7 | 68.9 |
| No-Vac. no exp Cont | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 100.0 | 100.0 |
| Experiment 17.6 | | | | | | | | | | |
| no vac-exp. | 99.4 | 98.9 | 96.1 | 92.8 | 87.8 | 82.2 | 77.8 | 70.6 | 61.1 | 51.1 |
| vac-exp. | 99.4 | 98.9 | 96.1 | 94.4 | 89.4 | 84.4 | 81.1 | 77.2 | 71.7 | 65.6 |
| No-Vac. no exp Cont | 100.0 | 100.0 | 100.0 | 100.0 | 100.0 | 100.0 | 100.0 | 100.0 | 100.0 | 100.0 |
| vac-no exp. | 98.3 | 98.3 | 98.3 | 98.3 | 98.3 | 96.7 | 96.7 | 96.7 | 96.7 | 96.7 |
| Experiment 17.7 | | | | | | | | | | |
| no vac-exp. | 98.3 | 98.3 | 97.8 | 96.7 | 89.4 | 82.2 | 73.3 | 64.4 | 55.6 | 47.2 |
| vac-exp. | 99.4 | 98.9 | 97.8 | 95.6 | 91.1 | 85.0 | 76.1 | 72.2 | 67.2 | 61.1 |
| No-Vac. no exp Cont | 100.0 | 98.3 | 98.3 | 98.3 | 98.3 | 98.3 | 98.3 | 98.3 | 98.3 | 98.3 |
| vac-no exp. | 100.0 | 100.0 | 100.0 | 100.0 | 100.0 | 100.0 | 100.0 | 100.0 | 100.0 | 100.0 |
| Experiment 17.8 | | | | | | | | | | |
| no vac-exp. | 100.0 | 99.4 | 98.9 | 95.6 | 84.4 | 78.9 | 70.6 | 64.4 | 57.2 | 48.3 |
| vac-exp. | 99.4 | 99.4 | 98.9 | 94.4 | 86.7 | 83.3 | 76.7 | 71.7 | 65.0 | 58.3 |
| No-Vac. no exp Cont | 100.0 | 100.0 | 100.0 | 100.0 | 100.0 | 100.0 | 100.0 | 100.0 | 100.0 | 100.0 |
| vac-no exp. | 100.0 | 100.0 | 100.0 | 100.0 | 100.0 | 100.0 | 100.0 | 100.0 | 100.0 | 100.0 |

The present invention is not to be limited in scope by the specific embodiments described herein.

Indeed, various modifications of the invention in addition to those described herein will become apparent to those skilled in the art from the foregoing description and the accompanying figures. Such modifications are intended to fall within the scope of the appended claims. It is further to be understood that all numerical values, provided for description, are approximate.

All patents, patent applications, publications, and other materials cited herein are hereby incorporated herein reference in their entireties. In case of conflicting terminology, the present disclosure controls.

BIBLIOGRAPHY

"CRC Handbook of Mariculture",1983, Vol. 1, CRC Press, Inc., Boca Raton.

"Laboratory Manual for the Culture of Penaeid Shrimp Larvae", 1993, Grandvil. D. Treece and Michael E. Yates, Texas A&M Sea Grant program TAMU-SG-88-202(R).

Arala-Chaves, M., Sequeira, T. 2000. Is there any kind of adaptive immunity in invertebrates? Aquaculture 191, 246–258.

Chang, P. S., Chen, L., Wang, Y. 1998. The effect of ultraviolet irradiation, heat, pH, ozone, salinity and chemical disinfectants on the infectivity of white spote syndrome baculovirus. Aquaculture 166: 1–17.

Flegel, T. W., Alday-Sanz, V. 1998. The crisis in Asian shrimp culture: current status and future needs. J. Appl. Ichthyol. 14: 269–273.

Flegel, T. W., Pasharawipas, T. 1998. Active viral accomodation: a new concept for crustacean response to viral pathogens. In Flegel, T. W. (Ed.) Advances in shrimp biotechnology. National Center for Genetic Engineering and Biotechnology, Bangkok. pp. 245–250.

Pasharawipas T., Flegel, T., Sriurairatana, S., Morrison, D. 1997. Latent yellow-head infections in Penaeus monodon and implications regarding disease tolerance or resistence. In T. W. Flegel, P. Menasveta and S. Paisarnat (Eds.). Shrimp Biotechnology in Thailand. National Center for Genetic Engineering and Biotechnology, Thailand. pp. 45–53.

Sahul Hameed, A. S., M. Anilkumar, M. L. Stephen Raj., Kunthala Jayaraman, 1998. Studies on the Pathogenicity of systemic ectodermal and mesodermal baculovirus and its detection in shrimp by immunological methods. Aquaculture 160, 31–45).

Supamattaya, K., Hoffman, R., Boonyaratpalin, S., Kanchanaphum, P. 1998. Experimental transmission of white spot syndrome virus (WSSV) from black tiger shrimp Penaeus monodon to sand crab Portunus palagicus, mud crab Scyla serrata and krill Acetes sp. Dis. Aquat. Org. 32: 79–85.

Venegas, C. A., Nonaka, L., Mushiake, K., Shimizu, K., Nishizawa, T., Muroga, K. 1999. Pathogenicity of penacid rod-shaped DNA virus (PRDV) to Kuruma prawn in different developmental stages. Fish Pathology 34(1): 19–23.

Patent Literature
U.S. Pat. No. 5,947,057 to Perez et al.
U.S. Pat. No. 5,732,654 to Perez et al.

What is claimed is:

1. A liquid tolerine composition comprising inactivated White Spot Syndrome Virus (WSSV).

2. A tolerine composition comprising inactivated virus in a solution having a pH of at least about 7.

3. The composition of claim 2, wherein the virus is in a solution having a pH of at least about 8.

4. The composition of claim 3, wherein the virus is in a solution having a pH of about 9.

5. The composition of claim 2, further comprising a dispersing agent.

6. The composition of claim 5, wherein the dispersing agent lowers the surface tension of the solution.

7. The composition of claim 2, further comprising a preservative.

8. The composition of claim 7, wherein the preservative is a bacteriostat or bactericide.

9. The composition of claim 8, wherein the preservative is selected from β-propiolactone, thimerosal, and propylene glycol.

10. The composition of claim 2, further comprising a virucide.

11. The composition of claim 10, wherein the virucide is also a bacteriostat.

12. A method of preparing a tolerine composition comprising inactivated virus, wherein the method comprises:

(i) filtering a homogenate of virus-infected tissue through a filter or screen;

(ii) allowing a precipitate to form in the first supernatant to produce a second supernatant; and (iii) isolating the second supernatant from the precipitate; wherein the virus is inactivated before or during any of steps (i) to (iii) and the second supernatant comprises inactivated virus.

13. The method of claim 12, wherein the virus is White Spot Syndrome Virus (WSSV).

14. The method of claim 12, wherein the tissue is shrimp tissue.

15. The method of claim 12, wherein the homogenate comprises about 30 to about 45 g of tissue.

16. The method of claim 12, wherein the cut-off size of the filter or screen is higher than about 105$\mu$.

17. The method of claim 16, wherein the cut-off size of the filter or screen is higher than about 150$\mu$.

18. The method of claim 12, wherein the first supernatant in step (i) is freeze-thawed to promote precipitation in step (ii).

19. The method of claim 12, wherein the second supernatant is isolated from the precipitate by at least one of centrifugation or filtration.

20. The method of claim 12, wherein the virus is inactivated by at least one of lowering the pH to 5.6 or below, irradiation, or a virucide.

21. The method of claim 20, wherein the virucide is also a bacteriostat.

22. The method of claim 12, further comprising adjusting the pH of the second supernatant to at least about 7.

23. The method of claim 22, wherein the pH is adjusted to at least about 9.

24. A method for inducing tolerance to a virus infection in shrimps, comprising the steps of:

(i) providing a tolerine composition comprising an inactivated virus in solution or suspension;

(ii) adding the tolerine composition to an aqueous solution comprising shrimp larvae; and (iii) exposing the shrimp larvae to the tolerine composition for at least about 30 minutes, wherein the tolerine composition is added in an amount effective to induce tolerance to the virus infection.

25. The method of claim 24, wherein the virus is White Spot Syndrome Virus (WSSV).

26. The method of claim 24, wherein the tolerine composition is prepared from autogenous viral material.

27. The method of claim 24, wherein the shrimp larvae are at a Z-1 developmental stage.

28. The method of claim 24, further comprising a step of mixing the shrimp larvae solution with the tolerine composition.

29. The method of claim 24, wherein the shrimp larvae are exposed to the tolerine for at least about 45 minutes.

30. The method of claim 24, wherein the added amount of tolerine is range 1 liter tolerine per 10–100 liters of shrimp solution.

* * * * *